United States Patent
Vincent

(10) Patent No.: US 12,380,991 B2
(45) Date of Patent: Aug. 5, 2025

(54) SYSTEMS AND METHODS FOR RENDERING IMAGES ON A DEVICE

(71) Applicant: FUJIFILM Healthcare Americas Corporation, Lexington, MA (US)

(72) Inventor: Brigil Vincent, Chapel Hill, NC (US)

(73) Assignee: FUJIFILM HEALTHCARE AMERICAS CORPORATION, Lexington, MA (US)

( * ) Notice: Subject to any disclaimer, the term of this patent is extended or adjusted under 35 U.S.C. 154(b) by 395 days.

(21) Appl. No.: 17/993,689

(22) Filed: Nov. 23, 2022

(65) Prior Publication Data

US 2024/0170131 A1    May 23, 2024

(51) Int. Cl.
| | |
|---|---|
| *G06T 17/00* | (2006.01) |
| *G06F 3/0487* | (2013.01) |
| *G06T 19/00* | (2011.01) |
| *G16H 30/20* | (2018.01) |
| *G16H 30/40* | (2018.01) |

(52) U.S. Cl.
CPC ........... *G16H 30/20* (2018.01); *G06F 3/0487* (2013.01); *G16H 30/40* (2018.01)

(58) Field of Classification Search
USPC ........................ 128/897–899, 920, 922–925; 345/418–441; 358/1.1–3.29, 1.11–1.18, 358/504–539, 480–485; 382/128–309; 600/300–312, 317, 340–342, 407–416, 600/473–477, 247–249, 921; 706/1–62, 706/900–903; 715/700–866, 200–277
See application file for complete search history.

(56) References Cited

U.S. PATENT DOCUMENTS

| | | | |
|---|---|---|---|
| 2007/0032720 A1* | 2/2007 | Koivukangas | A61B 5/7425 600/407 |
| 2012/0007866 A1* | 1/2012 | Tahan | G16H 30/20 345/428 |
| 2020/0310611 A1* | 10/2020 | Vincent | G09G 5/393 |

OTHER PUBLICATIONS

Boda Prakash; Systems and Methods for Caching Biological Image Data; 2020 (Year: 2020).*

* cited by examiner

*Primary Examiner* — Marcellus J Augustin
(74) *Attorney, Agent, or Firm* — Baker Botts L.L.P.

(57) ABSTRACT

Method for rendering images on a device, the method includes initiating an image viewing application operating on the device, downloading, in the image viewing application, a plurality of unrendered image files, wherein the plurality of unrendered image files are assigned a priority value based on when the plurality of image files are to be displayed, storing, in the image viewing application, the plurality of unrendered image files downloaded in at least one of a first device memory and a second device memory, where the plurality of unrendered image files are stored in the at least one of the first device memory and the second device memory according to the assigned priority value, rendering, in the image viewing application, the plurality of unrendered image files based on the assigned priority value using at least one device processor.

14 Claims, 14 Drawing Sheets

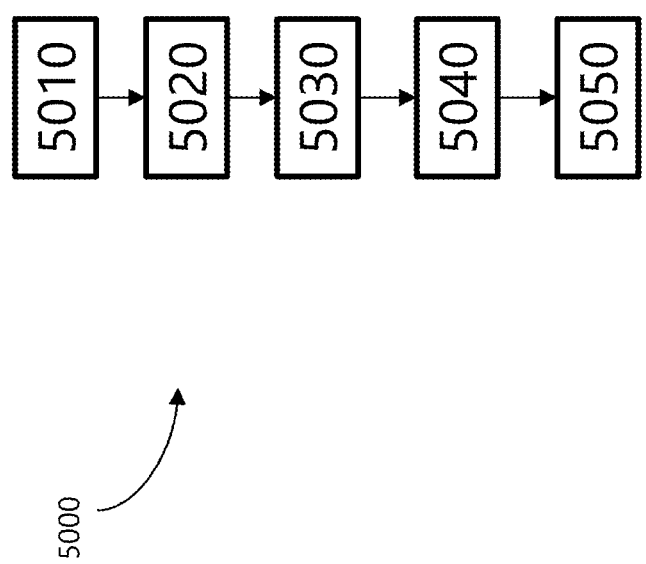

SYSTEMS AND METHODS FOR RENDERING IMAGES ON A DEVICE

BACKGROUND

Field of Disclosed Subject Matter

The disclosed subject matter is directed to systems and methods for downloading and rendering images on a device, for example, medical images, and more specifically, Digital Imaging and Communications in Medicine ("DICOM") Objects. The systems and methods described herein can utilize a combined server and device implementation to optimize performance in downloading and rendering images on a device.

Description of Related Art

In medical imaging, Picture Archiving and Communication Systems ("PACS") are a combination of computers and networks dedicated to the storage, retrieval, presentation, and distribution of images. While medical information can be stored in a variety of formats, a common format of image storage is DICOM. DICOM is a standard in which, among other things, medical images and associated meta-data can be communicated from imaging modalities (e.g., x-ray (or x-rays' digital counterparts: computed radiography ("CR") and digital radiography ("DR")), computed tomography ("CT"), and magnetic resonance imaging ("MRI") apparatuses) to remote storage and/or client devices for viewing and/or other use.

As an example, current image viewing applications can be built with server-side rendering technologies. This client-server model includes a server that can perform image rendering and a client application that can run in web browsers to display the images in the workstation client. The client application implementation is web based and hosted on web browsers. Implementation of advanced functionalities in web technologies and hosting them in web browsers comes with multiple challenges in providing the best experience when performing diagnostic reading of exams by radiologist and cardiologists.

Some of the challenges associated with this model can include network latency, which affects accurate high speed image visualization and navigation, and image rendering latency, which affects the accurate use of imaging tools. Additionally, browser-based web technologies impact the performance, smoothness and predictability of interactive image navigation/scrolling, particularly in high resolution diagnostic monitors. Browser-based web technologies further impact high speed and accurate playback of images in high resolution diagnostic monitors, such as Cine playback of DICOM images. These challenges, among others, can also reduce the ability to improve features for more advanced functionality.

Accordingly, there is a need for improved systems and methods for rendering images on a device.

SUMMARY

The purposes and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as the appended figures.

To achieve these and other advantages and in accordance with the purpose of the disclosed subject matter, as embodied and broadly described the disclosed subject matter is directed to systems and methods for rendering images on a device. For example, a method for rendering images on a device, the method includes initiating an image viewing application, downloading, in the image viewing application, a plurality of unrendered image files stored in a server memory, rendering, in the image viewing application, the plurality of unrendered image files using one or more device processors to generate a plurality of rendered image files; displaying, in the image viewing application, the plurality of rendered image files in at least one image window, and rendering, in the image viewing application, at least one server application in at least one native window container, the at least one server application is stored in the server memory and processed in one or more server processors.

The method can also include storing the plurality of unrendered image files in a device memory. The device memory can be at least one of in-memory cache and disk cache. The method can also include decompressing the plurality of unrendered image files prior to rendering. The method can also include rendering, in the image viewing application, the plurality of unrendered image files using the server processors until downloading the plurality of unrendered image files is complete. During the step of initiating the image viewing application, the at least one native window container can be initialized during application startup. Subsequent to the native window being initialized, the at least one server application can be rendered in the at least one native window container upon login by the user. The method can also include rendering, in the image viewing application, at least one second server application in a second native window container, where in the at least one second server application can be stored in a second server memory and processed in one or more second server processors. The at least one server application can include a web page. The plurality of unrendered image files can include DICOM images. The plurality of rendered image files can include multi-frame images.

In accordance with the disclosed subject matter, a system for rendering images on a device is provided. The system can include a server having one or more server processors and a server memory coupled to the server processors including instructions executable by the server processors, a device having one or more device processors and a device memory coupled to the device processors including instructions executable by the device processors. The device processors can be operable when executing the instructions to initiate an image viewing application, download, in the image viewing application, a plurality of unrendered image files stored in the server memory, render, in the image viewing application, the plurality of unrendered image files using the device processors to generate a plurality of rendered image files, display, in the image viewing application, the plurality of rendered image files in at least one image window, and render, in the image viewing application, at least one server application in at least one native window container, wherein the at least one server application can be stored in the server memory and processed in one or more server processors.

The device processors can also execute instructions to store the plurality of unrendered image files in the device memory. The device memory can be at least one of in-memory cache and disc cache. The device processors can also execute instructions to decompress the plurality of unrendered image files prior to rendering. The device processors can also execute instructions to render, in the image viewing application, the plurality of unrendered image files using the server processors until downloading the plurality of unrendered image files is complete. During the instruction to initiate the image viewing application, the at least one native window container can be initialized during application startup. Subsequent to the native window being initialized, the at least one server application can be rendered in the at least one native window container upon login by the user. The device processors can also execute instructions to render, in the image viewing application, at least one second server application in a second native window container. The at least one second server application can be stored in a second server memory and processed in one or more second server processors.

In accordance with the disclosed subject matter, a method for rendering images on a device is provided. The method can include initiating an image viewing application operating on the device, downloading, in the image viewing application, a plurality of unrendered image files are assigned a priority value based on when the plurality of image files are to be displayed, storing, in the image viewing application, the plurality of unrendered image files downloaded in at least one of a first device memory and a second device memory, where the plurality of unrendered image files are stored in the at least one of the first device memory and the second device memory according to the assigned priority value, rendering, in the image viewing application, the plurality of unrendered image files based on the assigned priority value using at least one device processor, where if the plurality of unrendered image files having a predetermined priority value need to be displayed before downloading has completed, the rendering occurs in at least one processor of a server electrically coupled to the image viewing application, and displaying the plurality of rendered image files, in the image viewing application, based on the assigned priority value, where the second device memory transfers at least one of the plurality of unrendered image files to the first device memory based on the assigned priority value and available storage space in the first device memory.

The assigned priority value can be at least two priority values to assign to the plurality of image files. The method can also include decompressing, in the image viewing application, the plurality of unrendered image files according to the assigned priority values and available storage space in at least one of the first device memory and the second device memory. The decompression of the plurality of unrendered image files can be performed in the at least one device processor based on processing availability of the at least one device processor. The plurality of unrendered images can be DICOM images. The plurality of unrendered image files can each include multiple frame images where each multiple frame image has multiple frames, where each multiple frame image is split into a plurality of single frame files, and where the plurality of single frame files are stored in at least one of the first device memory and the second device memory. The multiple frame images can be split into the plurality of single frame files by the at least one processor the server. The plurality of unrendered image files can be DICOM images.

In accordance with the disclosed subject matter, a system for rendering images on a device is provided. The system can include a server having one or more server processors and a server memory coupled to the server processors including instructions executable by the server processors, a device having one or more device processors and a device memory coupled to the device processors including instructions executable by the device processors. The device processors can be operable when executing the instructions to initiate an image viewing application operating on a device, download, in the image viewing application, a plurality of unrendered image files, where the plurality of unrendered image files are assigned a priority value based on when the plurality of image files are to be displayed, store, in the image viewing application, the plurality of unrendered image files downloaded in at least one of a first device memory and a second device memory, where the plurality of unrendered image files are stored in the at least one of the first device memory and the second device memory according to the assigned priority value, render, in the image viewing application, the plurality of unrendered image files based on the assigned priority value using at least one device processor, where if the plurality of unrendered image files having a predetermined priority value need to be displayed before downloading has completed, the rendering occurs in at least one processor of a server electrically coupled to the image viewing application, and display the plurality of rendered image files, in the image viewing application, based on the assigned priority value, where the second device memory transfers at least one of the plurality of unrendered image files to the first device memory based on the assigned priority value and available storage space in the first device memory.

In accordance with the disclosed subject matter, a method for rendering images on a device is provided. The method can include initiating an image viewing application operating on a device, downloading, in the image viewing application, at least one first unrendered image file, storing, in the image viewing application, the at least one first unrendered image file downloaded in at least one of a first device memory and a second device memory, rendering, in the image viewing application, the at least one first unrendered image file into an at least one first rendered image file using at least one device processor; and displaying the at least one first rendered image file, in the image viewing application, where the display of the at least one rendered image file is controlled through movement of a pointing device, wherein the image viewing application receives input data from the pointing device regarding movement of the pointing device.

The pointing device can be a mouse connected to the device. The movement of the pointing device can include one of at least a relative movement and an absolute movement of the pointing device. The plurality of unrendered image files can be assigned a priority value based on when the plurality of unrendered image files are to be displayed, wherein the plurality of unrendered image files are stored in the at least one of the first device memory and the second device memory according to the assigned priority value, and wherein the plurality of unrendered image files are rendered based on the assigned priority value. The image viewing application can track the movement of the pointing device to predict an at least one second unrendered image file to be displayed after the at least one first rendered image file. The method can include downloading, in the image viewing application, the at least one second unrendered image file, storing in the image viewing application, the at least one second unrendered image file downloaded in at least one of the first device memory and the second device memory, rendering, in the image viewing application, the at least one second unrendered image file into an at least one second rendered image file using the at least one device processor, and displaying the at least one second rendered image file, in the image viewing application. The image viewing application can be configured to scroll between the at least one first rendered image file and the at least one second rendered image file. The movement of the pointing device can include the scroll of a wheel. The image viewing application can be configured to transfer the at least one first unrendered image file from at least one of the first device memory and the second device memory.

In accordance with the disclosed subject matter, a system for rendering images on a device is provided. The system can include a server having one or more server processors and a server memory coupled to the server processors including instructions executable by the server processors, a device having one or more device processors and a device memory coupled to the device processors including instructions executable by the device processors. The device processors can be operable when executing the instructions to initiate an image viewing application operating on a device, download, in the image viewing application, at least one first unrendered image file, store, in the image viewing application, the at least one first unrendered image file downloaded in at least one of a first device memory and a second device memory, render, in the image viewing application, the at least one first unrendered image file into an at least one first rendered image file using at least one device processor, and display the at least one first rendered image file, in the image viewing application, where the display of the at least one rendered image file is controlled through movement of a pointing device, where the image viewing application receives input data from the pointing device regarding movement of the pointing device.

In accordance with the disclosed subject matter, a method for rendering images on a device is provided. The method can include initiating an image viewing application operating on a device, launching, in the image viewing application, a plurality of windows, the plurality of windows configured to run an image viewer window and at least one application window, and establishing, in the image viewing application, a settings relationship between the plurality of windows on the device, wherein the plurality of windows are assigned relationships configured to synchronize content across the plurality of windows, where the image viewer window can include a first communication interface registered to the at least one application window based on the settings relationship, where the at least one first application window comprises a first window container operated by the device and a first web interface layer operated by a first server electrically coupled to the device, where the image viewer window is operated by the device, and where the first communication interface is configured to operate within the device when communicating between the image viewer window and the first window container.

The first application window can be one of a server application window and an external application window. The server application window can be configured to run a server application and the external application window is configured to run an external application. The plurality of windows can include a second application window having a second window container operated by the device and a second web interface layer operated by one of the first server and a second server electrically coupled to the device. The image viewer window can include a second communication interface registered to the second application window. The second web interface layer, when communicating with the first web interface layer, operates within the device and operates within at least one of the first server and the second server electrically coupled to the device. The second application window can be one of a server application window and an external application window, where the server application window is configured to run a server application and the external application window is configured to run an external application.

In accordance with the disclosed subject matter, a method for rendering images on a device is provided. The method can include initiating an image viewing application operating on a device, launching, in the image viewing application, a first instance comprising a plurality of windows, the plurality of windows configured to run at least an image viewer window and an application window, establishing, in the image viewing application, a settings relationship between the plurality of windows on the device, wherein the plurality of windows are assigned relationships configured to synchronize content across the plurality of windows, launching, in the image viewing application, a second instance comprising a second plurality of windows, the second plurality of windows configured to run at least a second image viewer window and a second application window, and establishing, in the image viewing application, a second settings relationship between the second plurality of windows on the device, wherein the second plurality of windows are assigned relationships configured to synchronize content across the second plurality of windows, where the image viewer window comprises a first communication interface registered to the application window based on the settings relationship, where the second image viewer window comprises a second communication interface registered to the second application window based on the settings relationship, where switching from the first instance to the second instance hides the at least one application window and displays the at least one second window.

The application window and the second application window can both run a same application. The same application can be one of a server application, a device application, and an external application. The image viewing application can manage a memory cache to ensure that memory utilization is below a predetermined value. The image viewing application can communicate with a device application and wherein the image viewing application is configured to transfer data to the device application. The image viewing application can be configured to transfer images from the image viewing application to the device application. The method can include downloading data associated with at least the first instance such that image viewing can be performed while disconnected from the internet. The data associated with the first instance can include at least a plurality of image files. The data associated with the first instance can include at least one of user settings, Java script, HTML assets. The method can include downloading data associated with at least the second instance such that image viewing can be performed while disconnected from the internet. Switching from the first instance to the second instance can automatically save data associated with the application window to a device memory.

DRAWINGS

FIG. 14 is a flowchart illustrating a method for rendering images on a device, in accordance with the disclosed subject matter.

DETAILED DESCRIPTION

Reference will now be made in detail to various exemplary embodiments of the disclosed subject matter, exemplary embodiments of which are illustrated in the accompanying drawings. For purpose of illustration and not limitation, the systems and method are described herein with respect rendering images, and particularly, digital medical images (also referred to as "medical image"), specifically DICOM images. However, the methods and systems described herein can be used for rendering any digital images. As used in the description and the appended claims, the singular forms, such as "a," "an," "the," and singular nouns, are intended to include the plural forms as well, unless the context clearly indicates otherwise. Accordingly, as used herein, the term medical image can refer to one medical image, or a plurality of medical images. For example, and with reference to FIG. 1 for purpose of illustration and not limitation, as referred to herein a medical image record can include a single DICOM Service-Object Pair ("SOP") Instance (also referred to as "DICOM Instance" "DICOM image" and "image") 1 (e.g., 1A-1H), one or more DICOM SOP Instances 1 in one or more Series 2 (e.g., 2A-D), one or more Series 2 inside one or more Studies 3 (e.g., 3A, 3B), and one or more Studies 3. The DICOM image can have a photometric interpretation tag associated with the image. The photometric interpretation tag can identify, for example, that the image can be interpreted under Monochrome1, Monochrome 2, RGB, YBR Full, etc. The DICOM image can have a window center attribute. The DICOM image can have a window width attribute.

Figure 2:
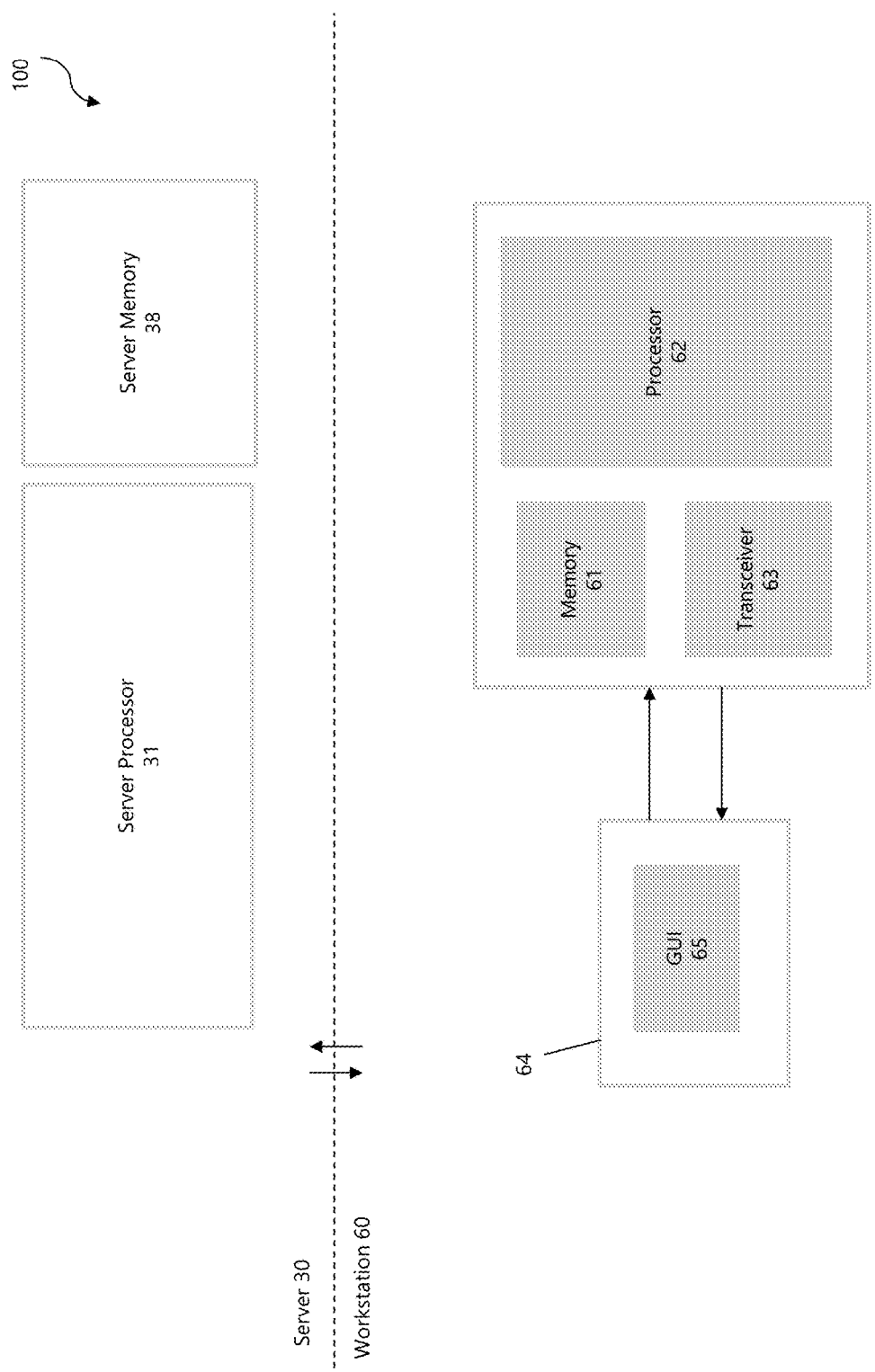
FIG. 2 shows the architecture of a system for rendering images in a device, in accordance with the disclosed subject matter.

Referring to FIG. 2 for purpose of illustration and not limitation, the disclosed system 100 can be configured to render digital images on a device. For example, system 100 can be configured to render digital images of a medical record, such as DICOM images 1 (e.g., 1A-1H). Particularly, system 100 can render the DICOM Images 1 1 (e.g., 1A-1H) such that the DICOM Images 1 (e.g., 1A-1H) display quickly and accurately, for making medical diagnoses. The system 100 can include one or more computing devices defining a server 30 and user workstation 60. The user workstation 60 can be coupled to the server 30 by a network. The network, for example, can be a Local Area Network ("LAN"), a Wireless LAN ("WLAN"), a virtual private network ("VPN"), or any other network that allows for any radio frequency or wireless type connection. For example, other radio frequency or wireless connections can include, but are not limited to, one or more network access technologies, such as Global System for Mobile communication ("GSM"), Universal Mobile Telecommunications System ("UMTS"), General Packet Radio Services ("GPRS"), Enhanced Data GSM Environment ("EDGE"), Third Generation Partnership Project ("3GPP") Technology, including Long Term Evolution ("LTE"), LTE-Advanced, 3G technology, Internet of Things ("IOT"), fifth generation ("5G"), or new radio ("NR") technology. Other examples can include Wideband Code Division Multiple Access ("WCDMA"), Bluetooth, IEEE 802.11b/g/n, or any other 802.11 protocol, or any other wired or wireless connection.

Workstation 60 can take the form of any known client device. For example, workstation 60 can be a computer, such as a laptop or desktop computer, a personal data or digital assistant ("PDA"), or any other user equipment or tablet, such as a mobile device or mobile portable media player. Server 30 can be a service point which provides processing, database, and communication facilities. For example, the server 30 can include dedicated rack-mounted servers, desktop computers, laptop computers, set top boxes, integrated devices combining various features, such as two or more features of the foregoing devices, or the like. Server 30 can vary widely in configuration or capabilities, but can include one or more processors, memory, and/or transceivers. Server 30 can also include one or more mass storage devices, one or more power supplies, one or more wired or wireless network interfaces, one or more input/output interfaces, and/or one or more operating systems.

A user can be any person authorized to access workstation 60 and/or server 30, including a health professional, medical technician, researcher, or patient. In some embodiments a user authorized to use the workstation 60 and/or communicate with the server 30 can have a username and/or password that can be used to login or access workstation 60 and/or server 30.

Workstation 60 can include GUI 65, display 64, memory 61, processor 62, and transceiver 63. Medical image records 1 (e.g., 1A-1H) received by workstation 60 can be processed using one or more processors 62. Processor 62 can be any hardware or software used to execute computer program instructions. These computer program instructions can be provided to a processor of a general purpose computer to alter its function to a special purpose, a special purpose computer, application-specific integrated circuit ("ASIC"), or other programmable digital data processing apparatus, such that the instructions, which execute via the processor of the workstation 60 or other programmable data processing apparatus, implement the functions/acts specified in the block diagrams or operational block or blocks, thereby transforming their functionality in accordance with embodiments herein. The processor 62 can be a portable embedded micro-controller or micro-computer. For example, processor 62 can be embodied by any computational or data processing device, such as a central processing unit ("CPU"), digital signal processor ("DSP"), ASIC, programmable logic devices ("PLDs"), field programmable gate arrays ("FPGAs"), digitally enhanced circuits, or comparable device or a combination thereof. The processor 62 can be implemented as a single controller, or a plurality of controllers or processors.

Workstation 60 can send and receive medical image records 1 (e.g., 1A-1H) from server 30 using transceiver 63. Transceiver 63 can, independently, be a transmitter, a receiver, or both a transmitter and a receiver, or a unit or device that can be configured both for transmission and reception. In other words, transceiver 63 can include any hardware or software that allows workstation 60 to communicate with server 30.

Transceiver 63 can be either a wired or a wireless transceiver. When wireless, the transceiver 63 can be implemented as a remote radio head which is not located in the device itself, but in a mast. While FIG. 2 only illustrates a single transceiver 63, workstation 60 can include one or more transceivers 63. Memory 61 can be a non-volatile storage medium or any other suitable storage device, such as a non-transitory computer-readable medium or storage medium. For example, memory 61 can be a random-access memory ("RAM"), read-only memory ("ROM"), hard disk drive ("HDD"), erasable programmable read-only memory ("EPROM"), electrically erasable programmable read-only memory ("EEPROM"), flash memory or other solid-state memory technology. Memory 61 can also be a compact disc read-only optical memory ("CD-ROM"), digital versatile disc ("DVD"), any other optical storage, magnetic cassettes, magnetic tape, magnetic disk storage or other magnetic storage devices, or any other physical or material medium which can be used to tangibly store the desired information or data or instructions and which can be accessed by a computer or processor. Memory 61 can be either removable or non-removable. While FIG. 2 only illustrates a single memory 61, workstation 60 can include one or more memories 61. The one or more memories 61 can be of the same type or different types (e.g., one RAM and one HDD).

Workstation 60 can display medical image records 1 (e.g., 1A-1H) on the display 64 through the GUI 65. The display 64 any device suitable to view the medical image records 1 (e.g., 1A-1H). For example, display 64 can be a light emitting diode ("LED") display or a liquid crystal display ("LCD"). Display 64 can be either integrated into workstation 60 such that workstation 60 is one device or a separate device connected by wires or wireless communication. While FIG. 2 only illustrates a single display 64, workstation 60 can include one or more displays 64. GUI 65 can be an image viewing application 100 (shown in FIGS. 3 and 4).

Server 30 can include one or more server processors 31. The one or more processors can be of any of the type discussed above regarding workstation processor 62. Server 30 can include one or more server memories 38. The one or more memories can be any of the type discussed above regarding workstation memory 61.

Figure 1:
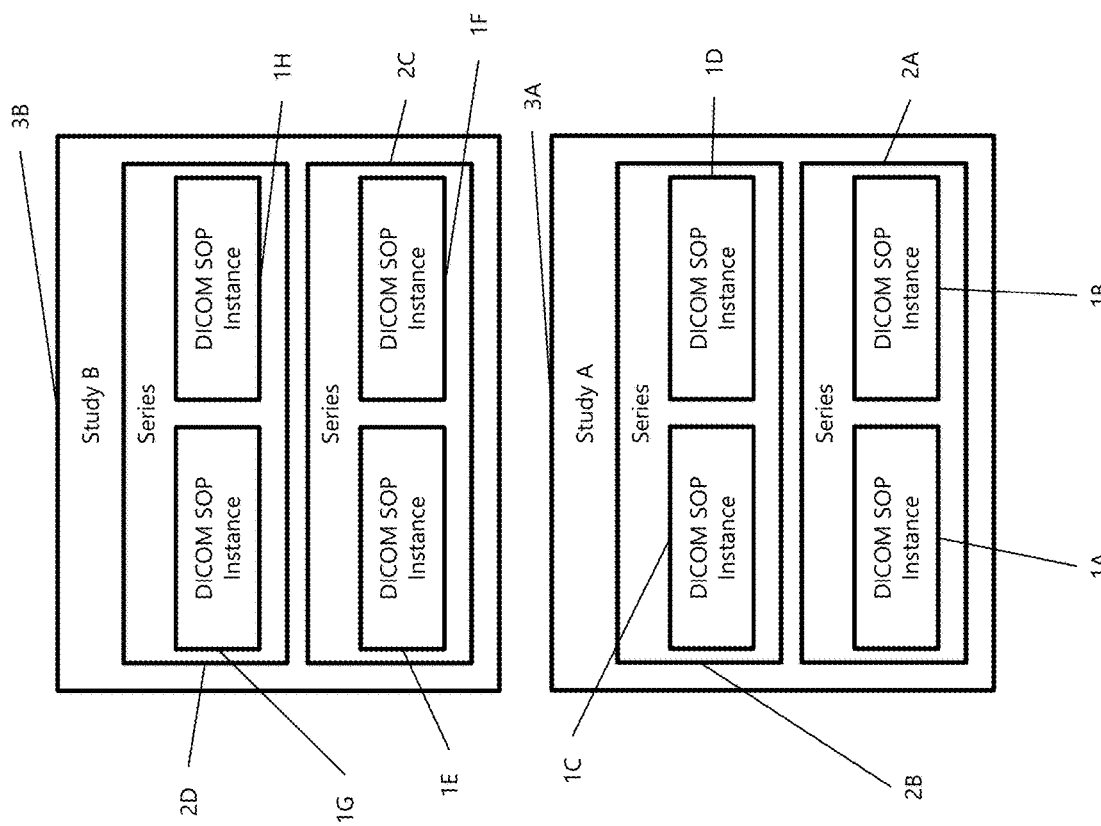
FIG. 1 shows a hierarchy of medical image records that can be rendered in accordance with the disclosed subject matter.
Figure 3:
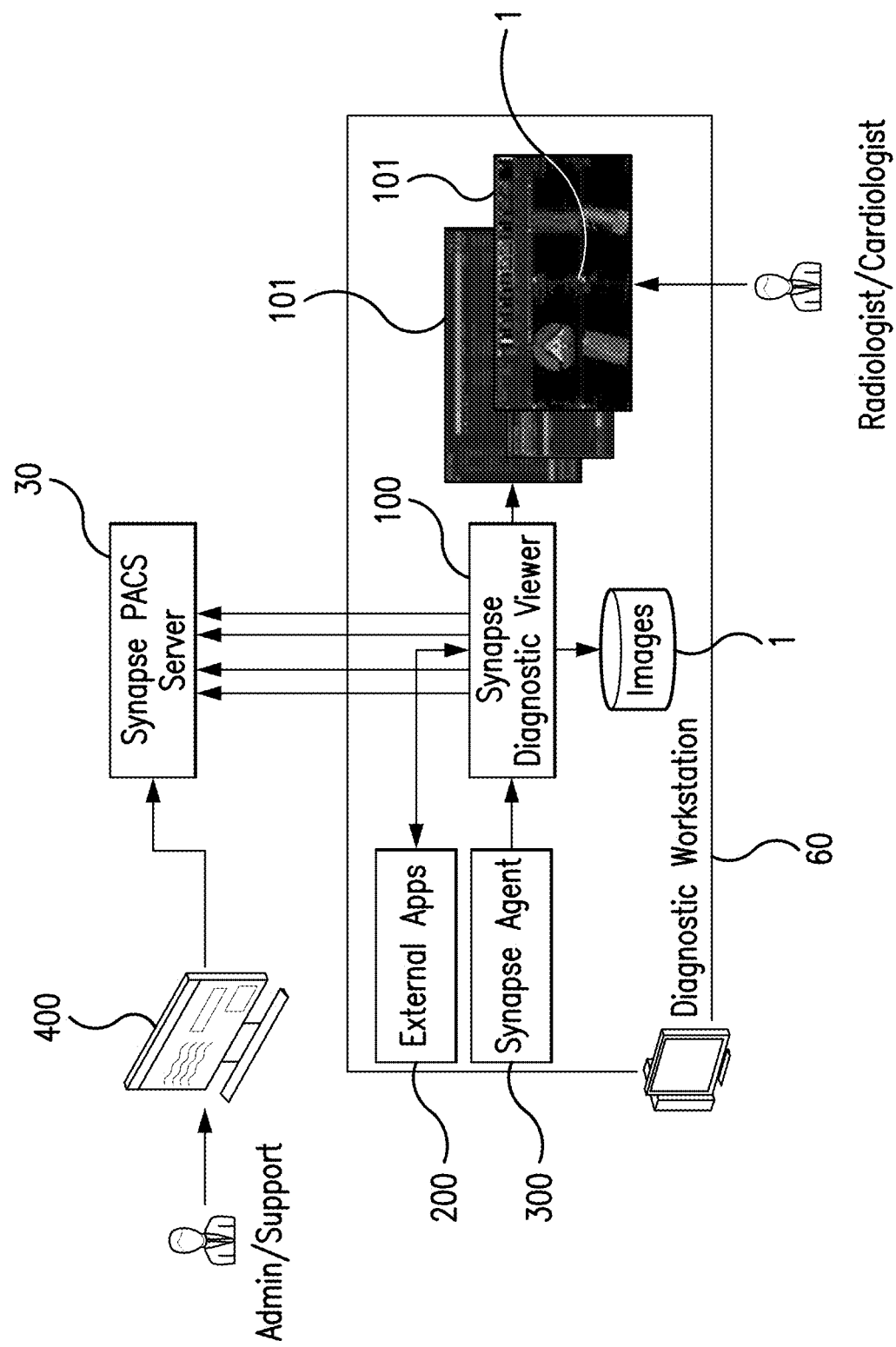
FIG. 3 shows the architecture of a system for rendering images in a device using an image viewing application, in accordance with the disclosed subject matter.
Figure 4:
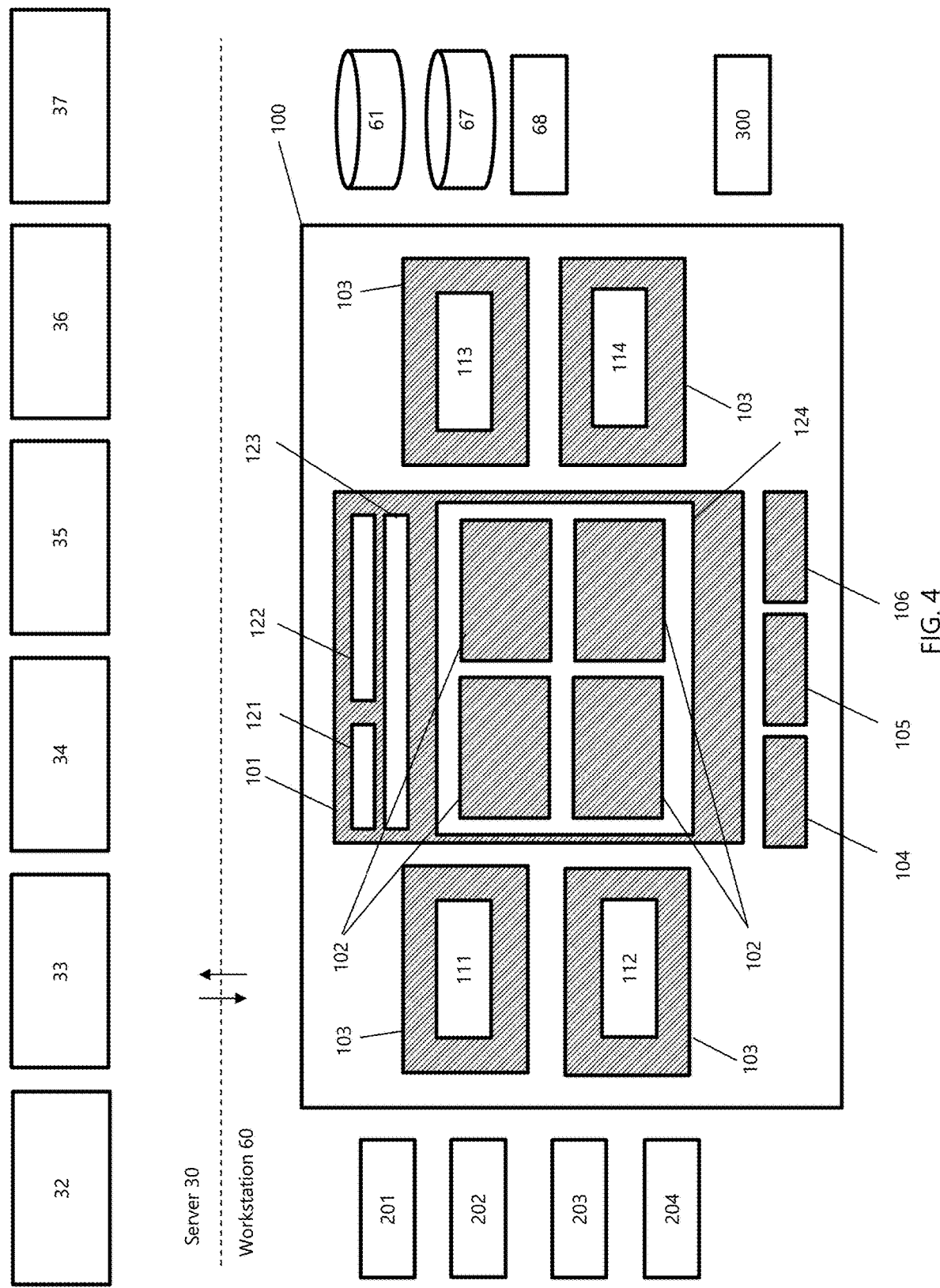
FIG. 4 shows the architecture of a system of an image viewing application, in accordance with the disclosed subject matter.

Referring to FIGS. 3 and 4 for purpose of illustration and not limitation, the image viewing application 100 (also referred to as Synapse diagnostic viewer 100) can be a native application deployed in workstation 60 (also referred to as diagnostic workstation 60) where the user interacts with the application and its contents to perform diagnostic reading of imaging studies 3 (e.g., 3A and 3B) shown in FIG. 1. Native can mean workstation 60 based, as opposed to, for example, server 30 based, or web based. The diagnostic viewer 100 is a hybrid application whose core implementation can be created with high performance cross-platform C++ technologies, or other suitable programming platforms, and it can be capable of rendering web pages hosted in the server 30 (which can also be referred to as Synapse PACS client or Synapse PACS server) thus combining the power of both native technologies and web technologies. C++ technologies are the most suitable for creating the diagnostic viewer 100 because, for example, C does not have an object oriented paradigm which is needed to design and develop larger systems, and C #and Java are not pure native because code compiled from C #or Java can require an interpreter layer between hardware and the program to run. Diagnostic viewer 100 operates best with being directly executable with hardware without another layer between the program and the hardware. Object C could be used, but would only be suitable in a MAC OS system. The native technologies can include resources of workstation 60. The resource of workstation 60 can include the following non-exhaustive list: workstation processors 62, workstation memory 61 (including RAM, hard disk storage, or any memory described above). The diagnostic viewer 100 can include the ability to host existing application web pages in its native window containers 103 and can allow the diagnostic viewer 100 to re-use the resources of workstation 60, while enhancing performance intuitive functionalities. The diagnostic viewer 100 can implement advanced functionalities using the resources of workstation 60. The diagnostic viewer 100 can include integration of external applications 200 (which can also be referred to as third party applications) having web pages hosted on an external server (not shown). The diagnostic viewer 100 can include integration of a Synapse Agent 300. The Synapse Agent 300 can be a light weight application with functions including: (1) maintaining lifetime of diagnostic viewer 100 by starting it when the user logs into the operating system; (2) maintaining login session based on the user's session; (3) performing housekeeping needs, such as clearing temporary internet file caches or clearing cached DICOM contents from disc (if any) during logoff or shutdown; (4) providing tray icon and context menu to perform operations such as launch application, login, logoff, configure data source, and shutdown; and (5) allowing operation of administrative tasks, including, for example, view current version, test compatibility with a data source for connection to the system, view current health, connectivity status, and performance benchmarks, upgrade latest version, and upload trouble shooting to server.

The diagnostic viewer 100 can re-use an existing web page based user interface that gives users the same application experience using diagnostic viewer 100 as when users launch a web browser based image viewing application (also referred to as Synapse Zero Viewer). While the existing web browser based image viewing application utilizes server-side rendering and transmitting image files through a network, the diagnostic viewer 100 can utilize a distributed computing paradigm by performing the rendering in workstation 60. While diagnostic viewer 100 can utilize resources of workstation 60 for its processing needs, the diagnostic viewer can also provide increased accuracy and performance without depending on latencies from a web browser or network.

Diagnostic viewer 100 can include one or more native window containers 103 to host each web page of the server 30 hosted application. In addition to this, diagnostic viewer 100 can include a workstation implementation for downloading and caching DICOM images 1 (e.g., 1A-1H) from server memory 38 to the workstation memory 61 or workstation cache 61, workstation rendering of the images, workstation implementation of imaging functionalities like image playback/scrolling, advanced imaging functionalities like volume rendering, advanced workflow functionalities like multi-study dictation, or any other suitable implementations. In general, any implementation which requires performance and precision beyond what a web implementation can offer can be operated by the workstation implementation.

The diagnostic viewer 100 can include one or more native window containers 103 which can render web pages 111, 112, 113, 114 of applications hosted in at least one of server 30 or a second server (not shown). By utilizing the native window container framework, the diagnostic viewer 100 eliminates the need to use third party browser applications to host applications hosted in server 30. The web pages can include Worklist 111, Power Jacket 112, Cardiology Advanced Reporting 113, Series Viewer Settings 114, integrated third party web pages (which can include third party worklist 201, clinical applications 202, reporting applications 203, and dictation systems 204), as well as other web pages not shown. For example, other window containers 103 can include home grown or third party web pages, including (1) home grown web pages that can be used to display radiologist/physician notes (for example about the examination), reports, or other related documents; (2) integrated third party vendor developed applications or web pages to display notes, reports, or documents; (3) integrated third party vendor clinical application to support reading of the study 3 (e.g., 3A and 3B); (4) integrated third party vendor reporting/dictation application to prepare or view reports; and (5) third party worklist or workflow applications.

Server 30 can include one or more server-based applications (e.g., 32 33, 34, 35, 36, 37) that are stored in the one or more server memories 38 and processed in the server 30 by the one or more server processors 31. The server-based applications can include Application UI 32, Study Service 33, Streaming Service 34, Image Rendering Service 35, Single-Sign On (SSO) 36, Administration Services 37, as well as other server applications not shown (e.g., DICOM Services, Administrative Services used for administration, monitoring and troubleshooting). Application UI 32 can include the Synapse Zero Viewer web application containing HTML/Java Script implementation of Image Viewer 124, Worklist 111, Power Jacket 112, Advanced Reporting 113, or other suitable programs, hosted in Synapse PACS server 30 which can be launched in Web Browser. Other examples of programs can include (1) Synapse Collaboration Chat; (2) User/Administrative settings UI; (3) Series Viewer (unlike Image Viewer 124 which is used for displaying entire study 3 (e.g., 3A and 3B), Series Viewer is only to visualize images from one series 2 (e.g., 2A-2D) of a study 3 (e.g., 3A and 3B) at a time); (4) Synapse Help Page; (5) DICOM Transfer/Media Burn UI that can be used to send DICOM images to another server capable of receiving DICOM images or burn DICOM images to media; and (6) Synapse 3D which is an application that can be used for advanced 3D visualization functionalities. Synapse Diagnostic Viewer 100 can render the same web implementations in its native window containers 103 to provide the same UI/UX experience to the user. Study Service 33 can provide study information to diagnostic viewer 100 for displaying imaging studies in the viewer 100. The study information can also be provided for displaying in Worklist 111 and Power Jacket 112. Streaming Service 34 can be used by diagnostic viewer 100 to download medical images 1 (e.g., 1A-1H) for local rendering. Diagnostic Viewer 100 can send one HTTP request per image 1 (e.g., 1A-1H) to download the image 1 (e.g., 1A-1H). In the case of a multi-frame image, Streaming Service 34 can perform frame splitting where diagnostic viewer 100 can send one HTTP request per frame and download the medical image 1 (e.g., 1A-1H) frame by frame. Image Rendering Service 35 can run in the Synapse Server 30 and can perform server side rendering for Zero Viewer 32. Synapse Diagnostic Viewer 100 can utilize this service to render images 1 (e.g., 1A-1H) when the corresponding DICOM images 1 (e.g., 1A-1H) are not downloaded to the workstation 60 but the image 1 (e.g., 1A-1H) is required to be displayed to an image viewport 102. SSO 36 can allow a user of the diagnostic viewer 100 to log in to the system. Administration services 37 can include a set of services to manage deployment, upgrade, monitoring, troubleshooting and serviceability of the diagnostic viewer 100.

Diagnostic Viewer 100 can include one or more native window containers 103 to host one or more web pages of the Synapse PACS server 30. For example, Worklist 111, Power Jacket 112 and other applications, not including Image Viewer 124, can be hosted into one of the native window containers 103 similar to how these web pages are rendered in a modern web browser. The Image Viewer 124 can also be hosted into a native image viewer window container 101, but since it can offer performance intuitive and accurate image processing and visualization, certain parts in this web page can be overridden with native implementation. Several parts of the Image Viewer 124 can be re-used from its web implementation. For example, Study List Grid 121 (which can show a list of all DICOM studies of the patient including the study 3 (e.g., 3A and 3B) currently being read and it's prior studies if any), Series Picker 122 (which can include a list of thumbnails displayed in horizontal order where each thumbnail represents a series 2 (e.g., 2A-2D) in the study 3 (e.g., 3A and 3B) opened in the Image Viewer 124), Viewer Toolbar 123 (which can include a UI to enable imaging tools during diagnostic reading), Context Menu (not shown) (which can include a UI to enable imaging tools during diagnostic reading), as well as various buttons and indicators. For example, a Reading Protocol Editor can be used to prepare/modify reading protocol to layout the prepared layouts when displaying a study 3 (e.g., 3A and 3B) in Image Viewer 124. Anywhere Series Picker, similar to Series Picker 122 shown in the top of the Image Viewer 124, is available to invoke anywhere in the Image Viewer 124 and can move around for convenience Thinklog panel can show results from AI and CAD algorithms used to analyze the Study 3 (e.g., 3A and 3B) or manual/CAD finding from the patient's prior studies. Image viewports 102 can be the regions where images 1 (e.g., 1A-1H) can be displayed for diagnostic reading. The web based implementation in existing Zero Viewer can be overridden with native image visualization implementation, for example, using C++.

Upon launching the diagnostic viewer 100 in workstation 60, the diagnostic viewer 100 can connect to server 30. The user can provide login information to the diagnostic viewer 100 to access the application. The user can then choose one or more imaging studies from Worklist 111 provided along with other server 30 hosted applications. During the launching of the diagnostic viewer 100, the diagnostic viewer 100 can begin initializing at least one native image viewer window container 101. During the login, the diagnostic viewer 100 can begin to render at least one web page in the at least one native image viewer window container 101 to allow one or more of the functions of the diagnostic viewer 100 to be available once the user is ready to view clinical contents. Once the user opens the clinical contents, such as a DICOM study 3 (e.g., 3A and 3B), the diagnostic viewer 100 can show the at least one native image viewer window container 101 to the user. This can help to quickly display and navigate through various application UIs to provide quick and efficient workflow to the user. In addition to this, because the at least one native image viewer window container 101 can display clinical contents, like DICOM studies 3 (e.g., 3A and 3B), completely before the least one native image viewer window container 101 is presented to the user, potential workflow ambiguities to the user can be eliminated by preventing partial states viewed by user.

When opening the clinical study 3 (e.g., 3A and 3B), diagnostic viewer 100 will begin downloading all images 1 (e.g., 1A-1H) in the study 3 (e.g., 3A and 3B) to the workstation 60 and maintain it in workstation cache 61. The workstation cache 61 can be composed of in-memory image cache (not shown) and disc cache (not shown). The in-memory part of the cache 61 can have an upper size threshold which can be calculated based on the configuration of the memory and available primary memory (i.e., free space available in the workstation 60 RAM) in the workstation 60. Auto-calculation can calculate space available to utilize based on the configuration of the workstation 60. For example, for a configuration using 3 GB as minimum memory and stretch capacity as 80%, then auto-calculation logic can determine to use a minimum of 3 GB and maximum up to 80% of the free space in RAM by making sure that 20% of the RAM space is available in the workstation 60 for other applications to run. This is a configurable percentage where particular workstations 60 can set a preferred percentage based on hardware available and other applications expected to run at the workstation 60. Once the size of the images 1 (e.g., 1A-1H) downloaded reaches the threshold, the remaining images 1 (e.g., 1A-1H) can be stored to the disc cache (not shown). The image caching makes sure the images 1 (e.g., 1A-1H) are available locally in the workstation 60 and that the diagnostic viewer 100 can render locally available images 1 (e.g., 1A-1H) in the workstation 60 itself without needing to access images 1 (e.g., 1A-1H) from server 30. This can accelerate performance of imaging functionalities, which can include cine playback, scrolling, and interactive imaging operations without network latency present in today's server-side image rendering. The downloading can be automatically initiated when opening the study 3 (e.g., 3A and 3B) in the diagnostic viewer 100. The user can also be able to subscribe to one or more clinical studies 3 (e.g., 3A and 3B) or one or more worklist folders in the Worklist 111 to perform the streaming and caching in the background so that the images 1 (e.g., 1A-1F) can be available in workstation 60 before the user opens the study 3 (e.g., 3A and 3B). Caching images 1 (e.g., 1A-1F) of a study 3 (e.g., 3A and 3B) includes caching of relevant prior study images 1 (e.g., 1A-1F) which can make sure relevant prior images 1 (e.g., 1A-1H) are also available locally. Relevant prior images 1 (e.g., 1A-1H) can be identified based on users reading protocol preferences. For example, a preference can be provided in the reading protocol configuration which can provide how many prior studies a user wants to compare to the study 3 (e.g., 3A and 3B). A set of rules can be provided to select relevant prior studies to use among available prior studies. The number of prior studies can be between 0 and 6, and rules to find relevant prior studies can include matching modality, procedure, date of procedure, or other related aspects of the study 3 (e.g., 3A and 3B) or prior studies. When a user opens a study 3 (e.g., 3A and 3B), if the rules are configured and diagnostic viewer 100 identified that prior studies exist, then the study 3 (e.g., 3A and 3B) will be presented to the user and diagnostic viewer 100 can automatically compare the study 3 (e.g., 3A and 3B) with the identified prior studies. Because diagnostic viewer 100 will provide the study 3 (e.g., 3A and 3B) and relevant prior studies during reading, a caching algorithm can use the preferences configured and pull relevant prior studies into workstation cache 61, in addition to the current study 3 (e.g., 3A and 3B), such that DICOM images of the prior studies are also available to quickly render and display.

The caching of images 1 (e.g., 1A-1F) of the clinical study 3 (e.g., 3A and 3B) can be assigned a priority value. As an example, the priority value can be one of five priority values. Priority-1 can be images 1 (e.g., 1A-1H) which are required to be displayed immediately will be considered as highest priority and they will be downloaded first. Priority-2 can include neighboring images 1 (e.g., 1A-1H) of the currently displayed image 1 (e.g., 1A-1H) in the image stack, and can be downloaded with the next highest priority as they will likely need to be displayed next; Priority-3 can be all other images 1 (e.g., 1A-1H) that belong to the DICOM series 2 (e.g., 2A-2D) (stack of images displayed together in the viewports) and can be downloaded next. Priority-4 can be the rest of the images 1 (e.g., 1A-1H) belonging to the study 3 (e.g., 3A and 3B) being diagnosed and any prior studies 3 (e.g., 3A and 3B) associated with the study 3 (e.g., 3A and 3B). Priority-5 can be images 1 (e.g., 1A-1H) from studies 3 (e.g., 3A and 3B) which are subscribed to in the Worklist 111 of image studies 3 (e.g., 3A and 3B) to be used next but they have not been opened yet in the diagnostic viewer 100 and can be considered as lowest priority.

The diagnostic viewer 100 can use the assigned priority value to make sure images 1 (e.g., 1A-1H) that will be displayed next can be available in the in-memory cache (also referred to as primary memory) and the least needed images 1 (e.g., 1A-1H) can remain in the disc cache (also referred to as secondary memory) until the least needed images 1 (e.g., 1A-1H) are required. The diagnostic viewer 100 can perform intelligent memory management to ensure the actively displayed images 1 (e.g., 1A-1H) and the images 1 (e.g., 1A-1H) to be displayed next will be available in primary memory and the diagnostic viewer 100 can exchange content between the primary memory and the secondary memory according to the priority and availability of the primary memory space designated to store cached DICOM images 1 (e.g., 1A-1H).

The images 1 (e.g., 1A-1H) in DICOM format can be in a compressed format using any of the DICOM supported compression format and thus the images 1 (e.g., 1A-1H) need to be decompressed before the images 1 (e.g., 1A-1H) can be rendered to displayable images 1 (e.g., 1A-1H). The diagnostic viewer 100 can perform an intelligent background decompression on images 1 (e.g., 1A-1H) which are needed next for display by honoring the above-mentioned priority order, as well as based on availability of designated memory space in the workstation cache 61 for storing decompressed pixel data. This can make image rendering quicker when images 1 (e.g., 1A-1H) are required to display in the viewport 102. The decompression can be performed by using multiple CPU cores in workstation 60 based on the compression technique used and the availability of the CPU cores in the workstation 60 at the point of decompression processing.

The images 1 (e.g., 1A-1H) can be multi-frame SOP class images, or multi-frame images, (e.g., TOMO, US, XA, etc.). In the multi-frame images, one image can include multiple frames in the image 1 (e.g., 1A-1H) which can make the image file relatively large. This can pose a challenge to download performance, as the user needs to wait for the downloading of the large multi-frame SOP class images to finish before starting to perform the functionalities of the diagnostic viewer (e.g., scrolling, cine playback, etc.). The diagnostic viewer 100 can download multi-frame SOP class images frame-by-frame to the workstation 60. The server 30 can perform frame splitting of the multi-frame image to allow the download of the multiple frames on a frame-by-frame basis. This can eliminate the possible need for extra wait time required for multi-frame SOP class images and it can provide the same initial display performance that of single-frame SOPs (e.g., CT, MR, CR/DX, etc.).

Diagnostic viewer 100 can create displayable images 1 (e.g., 1A-1H) from DICOM images 1 (e.g., 1A-1H) locally in the workstation using image processing and rendering algorithms, when the DICOM images 1 (e.g., 1A-1H) are available in workstation cache 61. This local rendering will help to make sure workstation 60 does not need to access server resource through network real time and thus provide better performance and predictability, especially in low bandwidth scenarios. Local rendering can also eliminate the need for additional compression, transmission and decompression before displaying the images 1 (e.g., 1A-1H), as both rendering and display of images 1 (e.g., 1A-1H) can occur within the address space of the diagnostic viewer process. The rendered pixel data can be in the same format in which it is required to be displayed in the viewport. The rendered pixel data format can be dynamically chosen based on the decompressed pixel channels in the DICOM image 1 (e.g., 1A-1H), for example, single channel images can be rendered to 16-bit display pixels whereas multi-channel images can be rendered to RGB display pixel format.

When the DICOM images 1 (e.g., 1A-1H) are still in compressed formats, diagnostic viewer 100 can automatically perform DICOM decompression to ensure decompressed pixels are available for rendering.

The image rendering of diagnostic viewer 100 can support not only regular 2D image rendering, as well as all required image processing, such as scaling, windowing, invert, flip, and rotate. Diagnostic viewer 100 can also support multi-planar reconstruction, multi-modality fusion, and volume rendering. Diagnostic viewer 100 can also offer various image processing techniques like automatic registration of anatomies between images 1 (e.g., 1A-1H) belonging to different frames of reference, height alignment of MG view pairs, among other techniques, such as pixel density calculation of the selected pixel in the image or selected region of interest in CT images, automatic calculation of breast boundary by eliminating non-breast tissues in mammogram images, and automatic segmentation of legions in images with respect to a given point of selection.

The diagnostic viewer 100 can be designed to perform image rendering locally at workstation 60 by utilizing workstation processing power at workstation 60. For example, diagnostic viewer 100 can establish distributed computing and eliminate the need to use server side rendering though a network. But when performing reading from remote location, the image downloading of the DICOM image files 1 (e.g., 1A-1H) from server 30 to workstation 60 can be slower. Accordingly, users can experience slower initial display performance and image scrolling performance when caching of images 1 (e.g., 1A-1H) to be displayed to the viewport 102 is still in progress. The diagnostic viewer 100 can have download priority management, as described above, to make sure available network bandwidth will be utilized to download a displayed series of images 1 (e.g., 1A-1H) before any other content, but this can still depend on the network speed and size of the image 1 (e.g., 1A-1H) files. To eliminate and/or reduce this remote reading or slow network issues, the diagnostic viewer 100 can perform server side rendering when the downloading and caching of corresponding image 1 (e.g., 1A-1H) is not yet finished. As an example, when DICOM images 1 (e.g., 1A-1H) are not yet available in workstation cache 61, diagnostic viewer can perform server side rendering by requesting server 30 to provide rendered displayable images 1 (e.g., 1A-1H) in a compressed format (e.g., PNG). The images 1 (e.g., 1A-1H) can be decompressed into device specific display format and displayed to the viewport. In addition to compressed images, DICOM header information can also be downloaded from the server 30 and decoded at workstation 60 to visualize overlay information on top of the image 1 (e.g., 1A-1H).

Before displaying rendered images to the viewport, diagnostic viewer 100 can prepare additional overlays to be displayed together with the image. Such overlays can include the text overlay containing multiple clinically relevant text and numeric information about the DICOM image and a scale marker which can help users to perform measurements and analysis. These overlays can be burned into the displayable image before the images are displayed to the viewport 102 to ensure the images displayed are stable without any flickering effect. Additionally, all images 1 (e.g., 1A-1H) belonging to the series 2 (e.g., 2A-2D) of images 1 (e.g., 1A-1H) can be displayed together without any possibility of mismatch. Once required layers are burned into the image 1 (e.g., 1A-1H), the diagnostic viewer 100 can present the image 1 (e.g., 1A-1H) into the viewport 102 so that user can view the image 1 (e.g., 1A-1H).

The diagnostic viewer 100 can calculate the viewport space with 100% DPI scaling instead of using different scaling. Such scaling can ensure the images 1 (e.g., 1A-1H) are rendered without losing image quality due to any DPI scaling of display devices. Additionally, or alternatively, the diagnostic viewer 100 can display calibration similar to existing browser operated viewers.

The diagnostic viewer 100 can synchronize the swapping of image frames with the monitor refresh rate of display 64 while the user navigates through the image stack (Series 2 (e.g., 2A-2D)). This synchronization can prevent that images 1 (e.g., 1A-1H) not displaying to the user due to a race condition between monitor hardware refresh clocking and CPU clocking. In a multi-monitor environment, e.g. a plurality of displays 64, refresh rates of each monitor can be honored individually in conjunction with the frame rate at which the image navigation is requested by the user.

Figure 5:
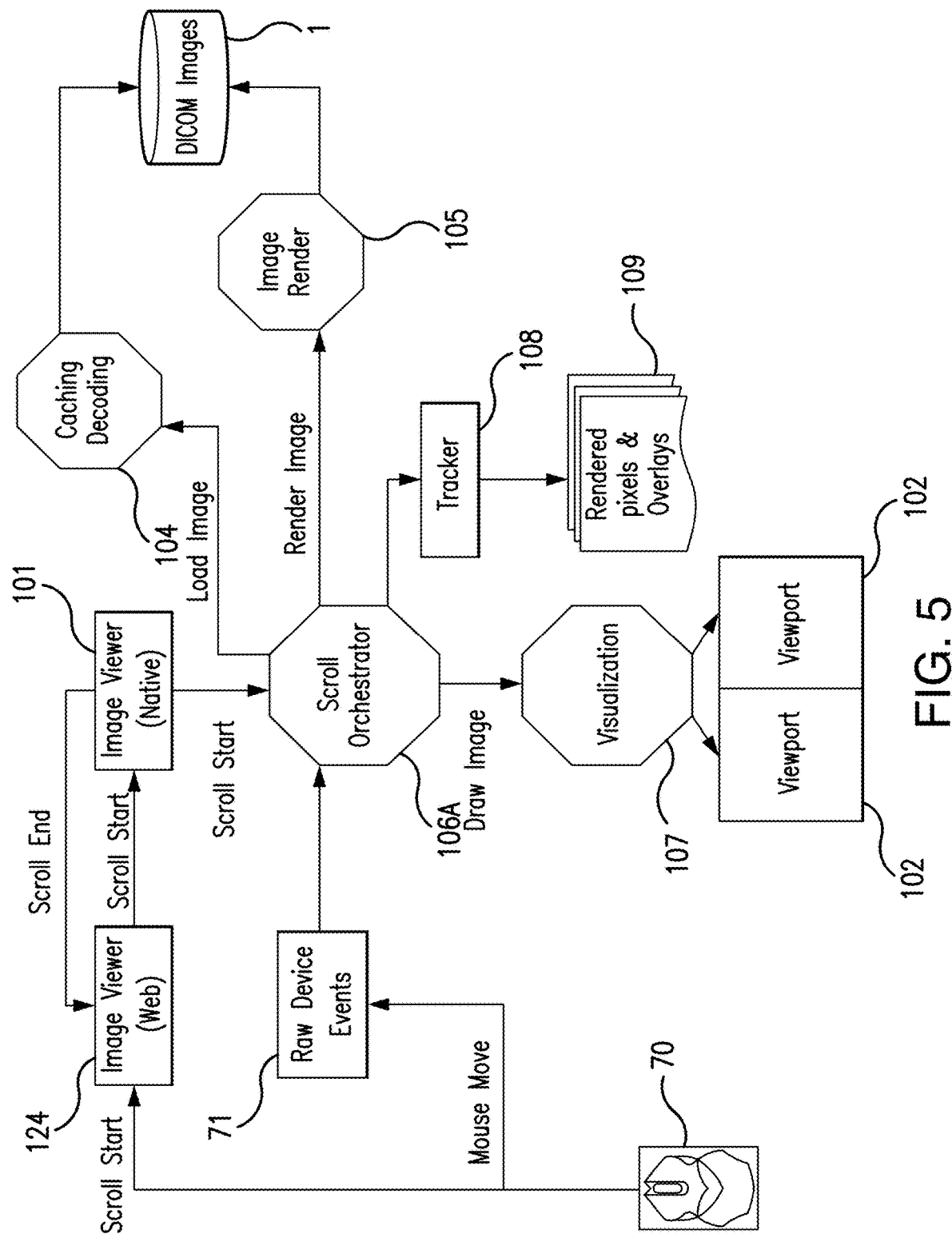
FIG. 5 shows the architecture of a system of an image viewing application for tracking mouse movement, in accordance with the disclosed subject matter.

Referring to FIG. 5 for purpose of illustration and not limitation, the diagnostic viewer 100 can allow the user to navigate through images 1 (e.g., 1A-1H) displayed in the viewport using mouse movement. There are three different modes at which the user can navigate through images 1 (e.g., 1A-1H) using mouse movement: (1) Precision Mode; (2) Standard Mode; and (3) Rapid Mode.

In Precision Mode, the user can navigate through the images 1 (e.g., 1A-1H) one by one without skipping any images 1 (e.g., 1A-1H) in the process. This non-skip mode navigation helps the user to perform precise visualization and analysis on anatomical regions in the image stack without missing any images 1 (e.g., 1A-1H).

In Standard Mode, the user can navigate through the images 1 (e.g., 1A-1H) with a frame rate associated with a speed of mouse movement of the user. When the mouse moves slowly, image navigation will follow the mouse slowly, as mouse movement becomes faster, the speed of navigation will also become faster. This mode can also ensure the user navigates through a smaller or medium or larger stack of images 1 (e.g., 1A-1H) with similar mouse mileage.

In Rapid Mode, the user can perform standard mode scroll with half of the mouse mileage required for Standard Mode.

To achieve the smoother and fully controlled navigation through the images 1 (e.g., 1A-1H) using mouse movement, a very precise mouse event handling is required. The diagnostic viewer 100 can acquire mouse events 71 directly from a mouse device 70 connected to the workstation 60 as a raw input which helps the diagnostic viewer 100 to track precise mouse movement by the user. This type of event handling can help to bypass other mouse event handlers in workstation 60 due to the fact that additional mouse tracking done in existing webpage layer implementation as HTML/javascript event handlers which should not interfere with precise event handling needs in the native layer. The diagnostic viewer 100 can process both relative and absolute movement of the mouse to ensure diagnostic viewer 100 can track the mouse device 71 precisely in all types of environments including a virtual desktop environment.

The image scrolling starts when the user initiates a dynamic scroll operation from the diagnostic viewer 100. In the Diagnostic Viewer, the web implementation 124 can pass the control to the native implementation 101 so that the native implementation 101 of dynamic scroll can take full control of the navigation to provide a premium image scrolling experience to the user.

Within the diagnostic viewer 100, a Scroll Orchestrator 106A engine can be a single threaded engine which orchestrates the scrolling operation. Upon starting the dynamic scroll, Scroll Orchestrator 106A can start to track mouse movements by monitoring the mouse events 71 from the mouse device 70, and can calculate scrolling parameters (e.g., direction, frame rate, the images to be displayed, anatomy to which the user intends to navigate to or stay around, and others) Scroll Orchestrator 106A can also track the historical mouse movements in order to ensure navigation can be accurately predicted and can perform processing tasks, such as rendering, upfront. When identifying images 1 (e.g., 1A-1H) to be displayed during each frame swap in the image scrolling, Scroll Orchestrator 106A will also identify related images 1 (e.g., 1A-1H) in the other viewports 102 by calculating various intelli-scroll evaluation criteria.

Intelli-scroll can provide the ability to scroll/navigate through active viewport where images displayed in other viewports will also get scrolled automatically with respect to the active viewport. There are various rules that can be provided to decide how other viewports get synchronously scrolling with active viewports. For example, "Orientation" mode synchronization (used mainly for CT/MR/PET studies) can scroll other viewport images with matching spatial plane where the image in the active viewport and other viewports has to be in the same plane (angle of spatial plane has to be the same or within 30 degree difference mutually) and spatial position in patient position irrespective of frame of reference. As used here, frame of reference means reference patient position when scanning took place. This is a type of special synchronization. "Frame of Reference" mode synchronization (used mainly for CT/MR/PET studies) is the same as "Orientation" mode except that both images have to be in the same frame of reference. This is also a type of spatial synchronization. "Sync by Index" mode (used in any modality) can synchronize images in other viewports by matching image index of the active viewport. "Synch by R-Wave" mode (used in ultrasound and x-ray multi-frames) can synchronize other viewports with active viewports using time vector so that heart rates or ECG signals always match. This is a type of temporal synchronization. "Synch by Prior" mode (used in mammogram studies) can provide stacking viewports where mammogram images belong to the current study and prior studies are displayed together and get scrolled with matching index. "XA Biplane" mode can provide each play of an x-ray biplane multi-frame image displayed side by side such that when the frame of one plane scrolls, corresponding frames of other planes also gets scrolled automatically. "Echo" mode can provide synchronization using the same technique as "Synch by R-Wave" mode but grouping different views and stages of ultrasound echo studies.

Within the diagnostic viewer 100, a Caching Decoding engine 104 can be a multi-threaded engine which can use the navigation information compiled by the Scroll Orchestrator 106A to ensure required images 1 (e.g., 1A-1H) are downloaded to the workstation cache 61, if they are not yet downloaded. Also, if the cached images 1 (e.g., 1A-1H) are in compressed format, the images 1 (e.g., 1A-1H) can be decoded into decompressed pixel data format to make rendering quicker. The order of caching and decoding can be based on the scrolling speed and direction predicted by the Scroll Orchestrator 106A.

Within the diagnostic viewer 100, an Image Render engine 105 can be a multi-threaded engine which can use the navigation information compiled by the Scroll Orchestrator 106A to render the images 1 (e.g., 1A-1H) required to be displayed to achieve image navigation. Image Render can perform image rendering using one or more processors 62 of workstation 60 based on priority. The priority can be decided by navigation information compiled by the Scroll Orchestrator 106A. As a non-limiting example, the image 1 (e.g., 1A-1H) required to be displayed can be rendered first, whereas a second image 1 (e.g., 1A-1H) required to be displayed can be rendered second, and images 1 (e.g., 1A-1H) likely required in the near future can be rendered third. The Image Render engine 105 can produce rendered pixel data and overlays 109 and store them in a tracker 108. In addition to the image 1 (e.g., 1A-1H) required to be displayed on the active viewport 102, images 1 (e.g., 1A-1H) required to be displayed on the other linked viewports 102 can be rendered and stored together in the tracker 108. This process can continue along with the navigation as all the images 1 (e.g., 1A-1H) cannot be kept in tracker 108 at a specific point of time as diagnostic viewer 100 has to manage memory utilization during scrolling. This can be based on the number of images that can be rendered in the background which is a value that can be calculated by Scroll Orchestrator 106A. The value can be calculated based on a value from configuration (for example, the default can be 64) and can be attributed with a size required for each rendered images in the memory and validated against the maximum number of rendered image cache, which can be another configured value (for example, the default can be 2 GB). At the specific point of time, tracker 108 will have an active image 1 (e.g., 1A-1H), a specific number of images 1 (e.g., 1A-1H) which are already displayed but required for potential quick reversal in the direction of image navigation and a specific number of images 1 (e.g., 1A-1H) which can be displayed in coming seconds in the direction of scroll.

Even though this process can ensure images 1 (e.g., 1A-1H) required to be displayed to the viewport 102 are available when navigation requires the images 1 (e.g., 1A-1H), there can be situations where images 1 (e.g., 1A-1H) are not available in the tracker 108. In such situation, high priority rendering can be triggered by the Scroll Orchestrator 106A for the image 1 (e.g., 1A-1H) and can render the images 1 (e.g., 1A-1H) immediately and display them to the viewport 102.

Within the diagnostic viewer 100, a Visualization Engine 107 can be a multi-threaded engine which takes care of drawing the image 1 (e.g., 1A-1H) and overlays 109 to the viewports 102. The Visualization Engine 107 can take rendered images 1 (e.g., 1A-1H) and overlays 109 from the tracker 108 and performs an off-screen rendering which creates a memory image of the viewport 102 by combining both the image 1 (e.g., 1A-1H) and overlay 109. Then the Visualization Engine 107 can draw the resultant off-screen image into the on-screen viewport 102. This can ensure there is no flickering effect during frame swap on the visual screen. This can also eliminate any possibility of mismatch in images 1 (e.g., 1A-1H) and overlays 109 presented to the viewport 102. This off-screen rendering can occur not only for the image 1 (e.g., 1A-1H) to be displayed in the active viewport 102, but for the images 1 (e.g., 1A-1H) required to be displayed on the linked viewport 102 and all updated viewports will be presented with new off-screen image together. Drawing the new image 1 (e.g., 1A-1H) to each viewport can be performed in parallel by Visualization Engine 107 where a dedicated one or more processors 62 of workstation 60 can be used to draw images 1 (e.g., 1A-1H) to each viewport 102. This can eliminate any possibility of any mismatched images 1 (e.g., 1A-1H) displayed on linked viewports and also makes sure all required viewports gets updated together, thereby providing best experience in intelli-scroll.

There are various intelli-scrolling criteria that diagnostic viewer 100 can offer which can include, but is not limited to, index synchronization (multiple viewports can be scrolled together by synchronizing them by image index), Frame Of Reference synchronization (multiple viewports can be scrolled together by identifying matching spatial images 1 (e.g., 1A-1H) with respect to the image 1 (e.g., 1A-1H) displayed in the active viewport but only for images 1 (e.g., 1A-1H) with same frame of reference), orientation synchronization (multiple viewports can be scrolled together by identifying matching spatial images 1 (e.g., 1A-1H) with respect to the image 1 (e.g., 1A-1H) displayed in the active viewport but only for images 1 (e.g., 1A-1H) with same spatial orientation) and other suitable intel-scroll features, for example, as described above.

Figure 6:
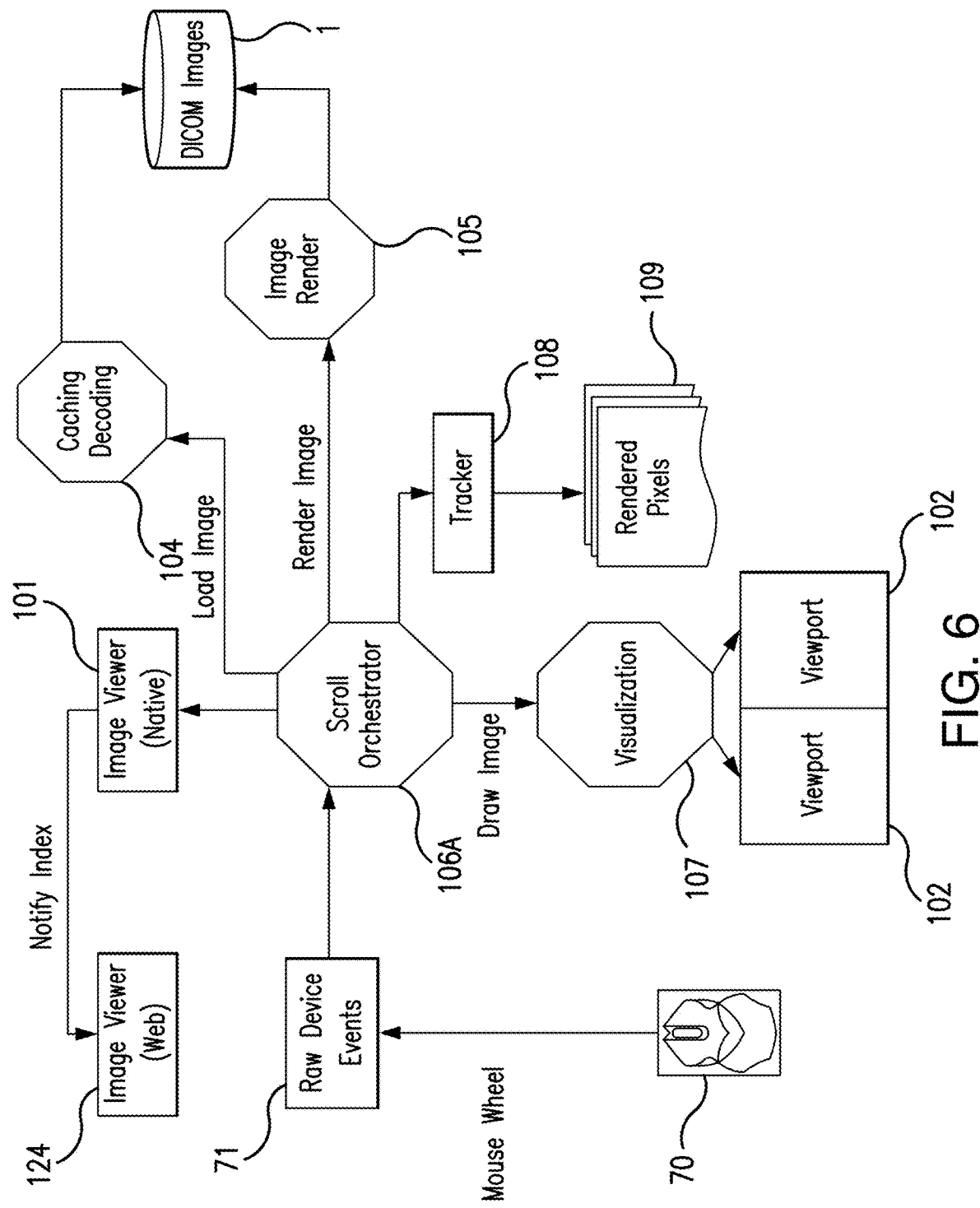
FIG. 6 shows the architecture of a system of an image viewing application for tracking mouse wheel scrolling, in accordance with the disclosed subject matter.

Referring to FIG. 6 for purpose of illustration and not limitation, the diagnostic viewer 100 can also allow the user to navigate through images 1 (e.g., 1A-1H) displayed in the viewport 102 using mouse 70 wheel movement. There are four different modes at which user can navigate through images 1 (e.g., 1A-1H) using mouse movement: (1) Legacy Mode; (2) Lightening Mode; (3) Dual Mode; and (4) Adaptive mode.

In Legacy Mode, the user can navigate through images 1 (e.g., 1A-1H) one by one per wheel notch movement. In this mode, irrespective of the intensity of the mouse wheel rotation, the navigation always corresponds to one image 1 (e.g., 1A-1H) per wheel notch movement which allows user to navigate through anatomy precisely.

In Lightening Mode, the user will be able initiate an image playback with respect to the speed of mouse wheel movement. For example, navigation of images 1 (e.g., 1A-1H) can be performed with a specific frame per seconds which is typically 60 fps.

In Dual Mode, the user can combine the functionality of both Legacy Mode and Lightening mode. For example, the user can rotate mouse wheel notch-by-notch to perform per notch image navigation slowly or rotate mouse wheel continuously in order to change to the playback mode as in the Lightening Mode.

In Adaptive Mode, the user can navigate through images 1 (e.g., 1A-1H) one by one slowly by rotating the mouse wheel notch by notch. The user can also accelerate the navigation by starting to accelerate the mouse wheel rotation which can typically provide 10 fps image navigation. The user can increase speed and continuity of the mouse wheel rotation to get to 15 fps, 30 fps, 45 fps, 60 fps and so on. Similarly reducing the speed and continuity of the mouse wheel rotation can bring the fps down. Adaptive Mode offers accurate navigation control with respect to the mouse wheel movement.

The image scrolling can start when the user starts to rotate a mouse wheel by focusing on a viewport 102. In the diagnostic viewer 100, the web implementation 124 can be silent and the native implementation 101 of wheel scroll can take full control of the navigation to provide a premium image scrolling experience to the user.

Similar elements in FIG. 6 have like numbers and can include all the features described above with respect to FIG. 5

Figure 7:
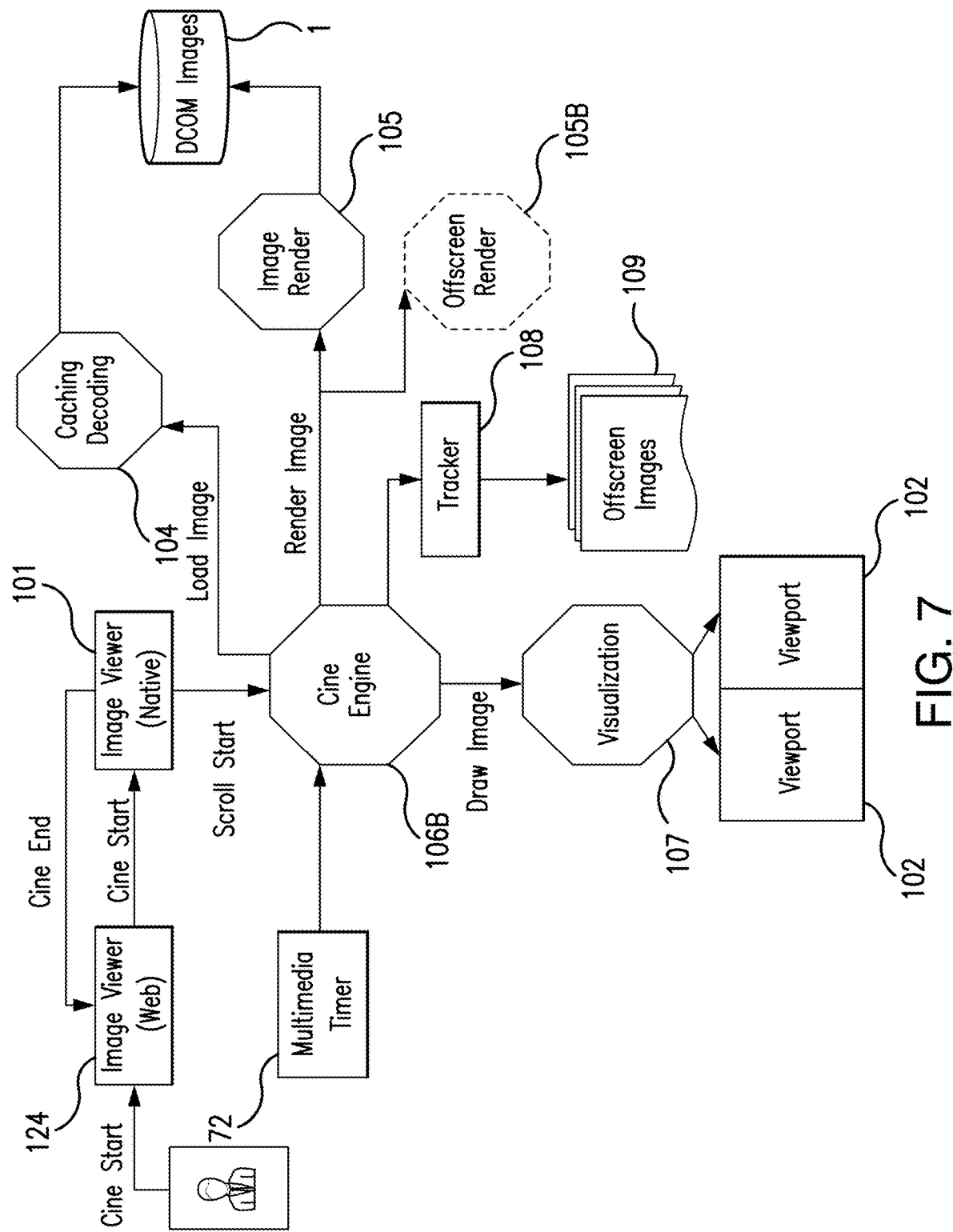
FIG. 7 shows the architecture of a system of an image viewing application for providing Cine playback, in accordance with the disclosed subject matter.

Referring to FIG. 7 for purpose of illustration and not limitation, the diagnostic viewer 100 can allow the user to perform image playback on a DICOM series 2 and can provide the ability to input the playback speed in the unit of frames per seconds. There can be various types of playback mode that are supported by the diagnostic viewer 100: (1) Loop Playback; (2) Oscillation Playback; and (3) Independent Playback.

Loop Playback can start from the current image 1 (e.g., 1A-1H) and continue to the last image 1 (e.g., 1A-1H) in the viewport and then start a next loop from the first image 1 (e.g., 1A-1H). This can continue until the user stops the playback or changes the playback mode to oscillation.

Oscillation Playback can start from the current image 1 (e.g., 1A-1H) and continue to the last image 1 (e.g., 1A-1H) in the viewport 102 and then perform playback in a reverse direction from the last image 1 (e.g., 1A-1H) to the first image 1 (e.g., 1A-1H). This can continue until the user stops the playback or changes the playback mode to loop.

Independent Playback can allow each viewport 102 to adjust its own playback speed in the unit of frame per seconds.

To achieve the accurate playback with precise frame per seconds per viewports 20, a very precise animation event is required to hit the processor every configured intervals. Cine Engine 106B can have a high precision multimedia timer 72 which can precisely hit its timer procedure every milliseconds, which gives the Cine Engine 106B the ability to perform playback with accurate frame rate. This can be achieved by setting up a timer which can be synchronized with a CPU counter and the timer can be set to hit every millisecond when the CPU counter counts to each 1 milliseconds. When CPU clocking to each 1 millisecond, to make sure the diagnostic viewer 100 won't miss the counter hit even when the application thread is busy with other operations, the diagnostic viewer 100 can use a dedicated thread to listen to CPU clocking and a queue to which each 1 millisecond clocking can be pushed to. This way, the diagnostic viewer 100 will be able to keep track of 1 millisecond intervals accurately.

Cine playback can start when user initiates playback from the diagnostic viewer 100. Cine playback can also start upon initial display of the diagnostic viewer 100, if it is configured to do so, based on study modality. In the diagnostic viewer, playback will be orchestrated by Cine Engine 106B in native implementation 101. Cine Engine 106B can start the multimedia timer 72 and can calculate the playback parameters like direction, frames per seconds needed for each viewport, images 1 (e.g., 1A-1H) needed to be displayed in each viewport 102 for each frame swap for every animation intervals etc.

The Caching-Decoding engine 104 can use the playback information compiled by Cine Engine 106B to make sure required images 1 (e.g., 1A-1H) are downloaded to the workstation cache 61, if they are not yet downloaded. Similar elements in FIG. 7 have like numbers and can include all the features described above with respect to FIG. 5

Diagnostic viewer 100 can include several synchronous playback criteria, such as index synchronization (multiple viewports can be played together by synchronizing them by image index), frame of reference synchronization (multiple viewports can be played together by identifying matching spatial images 1 (e.g., 1A-1H) with respect to the image 1 (e.g., 1A-1H) displayed in the active viewport but only for images 1 (e.g., 1A-1H) with same frame of reference), orientation synchronization (multiple viewports can be played together by identifying matching spatial images 1 (e.g., 1A-1H) with respect to the image 1 (e.g., 1A-1H) displayed in the active viewport but only for images 1 (e.g., 1A-1H) with same spatial orientation), or other suitable playback criteria. The diagnostic viewer 100 can include independent playback with different frames per seconds speed per viewport 102, synchronization by R-wave, Echo playback, Biplane playback, DSA playback based on the modality, and other suitable playback criteria. DSA is a technique of blending an x-ray contrast frame with a mask frame from the same x-ray multi-frame image where mask and contrast frames are specified in the DICOM header of the image based on how they are acquired by the x-ray scanner. While scrolling, diagnostic viewer 100 can make sure that masks and contrasts are always blended together and visualized together when DSA mode is turned on. If DSA mode is turned off, mask and contrast images can be displayed as independent frames in the image stack.

Cine Playback can have a maximum speed of 60 fps in the monitor with 60 Hz refresh rate. Cine Playback can also have a maximum speed of 120 fps in the monitor with 120 Hz refresh rate. Cine Playback can also have skippable mode playback where the maximum speed can go beyond monitor refresh capability.

The diagnostic viewer 100 can perform image rendering on a workstation 60 having multiple high resolution monitors 64 (6 Mega Pixels or higher). Each monitor 64 can include large 1-up viewports 102 where images 1 (e.g., 1A-1H) are displayed. The monitors 64 can achieve 60 fps while performing playback in the multiple monitors 64 synchronously, but the monitors 64 can have the frame rates drop to an achievable maximum fps of 30 or 40. In order to overcome this limitation, without using a graphics processing unit (GPU), the diagnostic viewer 100 can have an emulated GPU rendering technique which is called Off-screen Render engine 105B. Off-screen Render engine 105B can pre-allocate one or more image memory matches with the viewport size and perform off-screen drawing of images 1 (e.g., 1A-1H) using one or more dedicated processors 62 of workstation 60. This in-memory off-screen rendering can happen after the Image Render engine 105 finishes rendering and before the Visualization Engine 107 displays them to screen. This can allow the display of images 1 (e.g., 1A-1H) quicker than usual and the Visualization Engine 107 will be able to draw images 1 (e.g., 1A-1H) to the screen more quickly. As this process requires having one or more dedicated processors 62 reserved for this processing and this additional step is required only when there are multiple high resolution diagnostic monitors used with multiple large 1-up viewports, the diagnostic viewer can turn the Off-screen Render engine 105B ON or OFF based on the need and availability of required hardware.

Similar to scrolling and cine playback, there are several other image viewer 124 features that have overridden implementation in native side in order to provide premium experience to the user for the diagnostic reading of imaging study 3 (e.g., 3A and 3B) including Image Slider, Reference Lines, and Active Overlay.

Image Slider: A slider bar is provided in each viewports 102 where there are more than 10 images 1 (e.g., 1A-1H) in the viewport. The slider bar can help the user to perform image navigation and also convey the relative location of the current image 1 (e.g., 1A-1H) within the image stack. As web implementation of the image slider affects scrolling/playback performance, the diagnostic viewer has native implementation of the image slider.

Reference Lines: Reference Lines are the lines displayed in viewports to indicate relative spatial position of the images 1 (e.g., 1A-1H) displayed in the linked viewports with respect to image 1 (e.g., 1A-1H) displayed in the focused viewport. As display of these lines based on web implementation affects scrolling/playback performance, the diagnostic viewer has native implementation of the reference line visualization.

Active Overlay: Some fields in the text overlays are interactive and the user can perform different operations by clicking on the text overlay field like changing window level or scaling. As diagnostic viewer implementation of text overlays are in native layer, active overlays also implemented in native layer.

Figure 8:
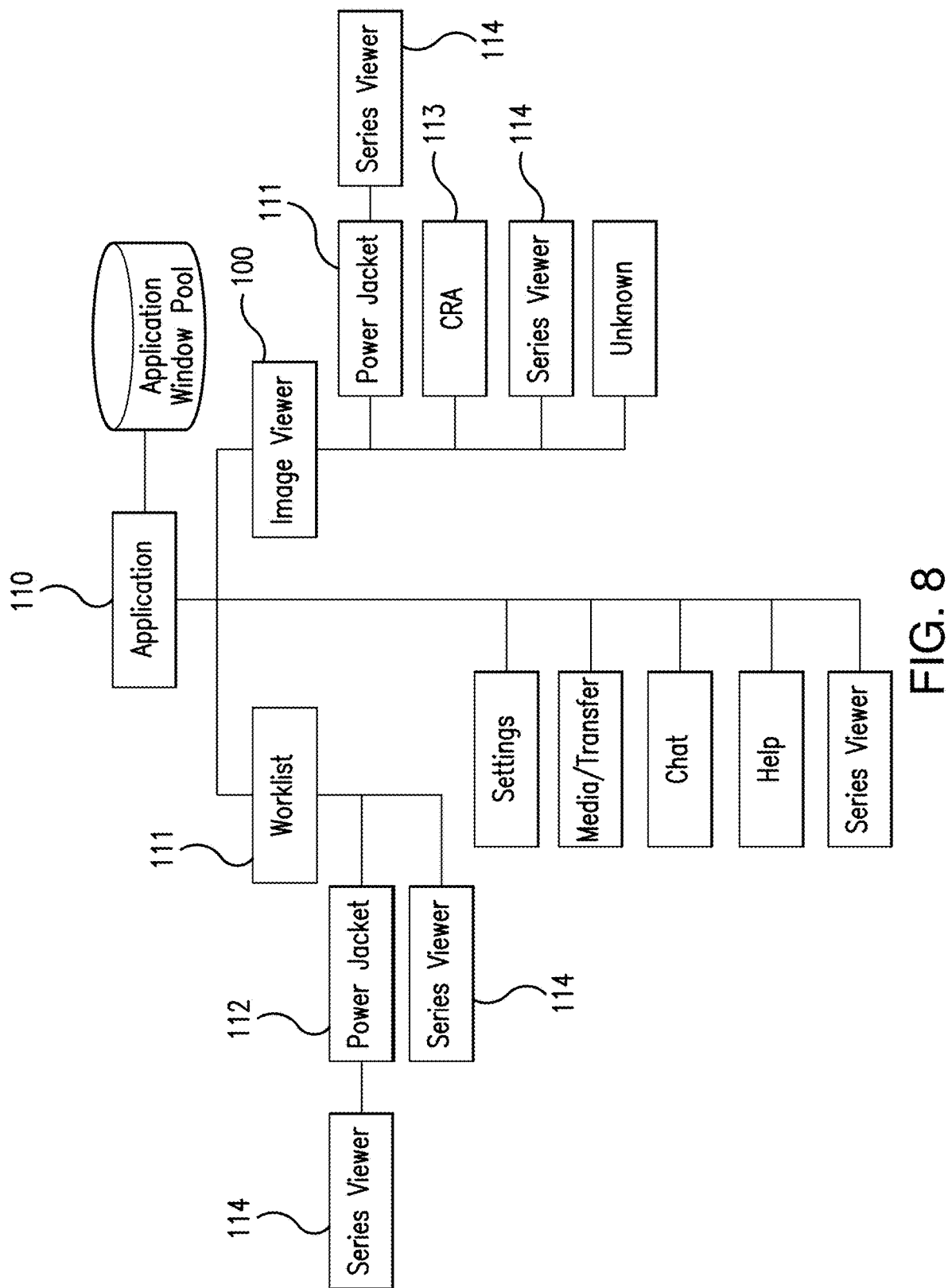
FIG. 8 shows the architecture of a system of an image viewing application for managing integrated applications into the image viewing application, in accordance with the disclosed subject matter.

Referring to FIG. 8 for purpose of illustration and not limitation, the diagnostic viewer 100 can have various application windows for running applications (e.g., Worklist 111, Power Jacket 112, Image Viewer 124, Advanced Reporting 113, User Settings 114, Series Viewer (not shown), or other suitable applications). Managing and coordinating these different windows is the key to establishing various reading workflow and at the same time to ensure information displayed in each window is accurate without any chance for mismatch. The existing browser viewer launches each of these windows as decoupled browser windows and utilizes browser local storage as a means to store active clinical content information and local storage events used to send messages across different windows. This always poses performance challenges, timing issues and race conditions. The diagnostic viewer 100 maintains each of these windows as native window container 103 of same application process can set appropriate parent-child relationships between these windows, and can allow them to communicate and exchange clinical information to each other without ambiguity.

The diagnostic viewer 100 can maintain a pool of pre-initialized windows and, based on content launched by the user, the diagnostic viewer 100 can present the required window or window groups. The diagnostic viewer 100 can set relationships between the windows (by registering a communication interface between related windows). The relationships can allow the context synchronizing between window groups using their relationship itself and can eliminate the need to have additional mechanisms, such as browser local storage, to synchronize the various windows to prevent information mismatch. For example, the diagnostic viewer 100 can have a window pool from which the diagnostic viewer 100 can pick a viewer window and display content of a newly opened study 3 (e.g., 3A and 3B). The view windows taken from the pool can have already been used in the past for displaying another study 3 (e.g., 3A and 3B) in the past. Once pushed back into a window pool, the window pool can reload the user interface so that none of the content from the previously displayed study 3 (e.g., 3A and 3B) will be present in the view window and the study content shown in the view window is removed. When the window pool doesn't have a viewer window in use, the diagnostic viewer 100 can create a new window to display the content of a newly opened study 3 (e.g., 3A and 3B).

Having all of the application windows within the same native process can create a high performance and highly predictable/accurate communication mechanism between multiple windows of the diagnostic viewer 100. The diagnostic viewer can ensure clinical context is always accurately synchronized between application windows, thereby eliminating any possibility to patient safety challenges. In addition to synchronizing multiple application windows, diagnostic viewer 100 also synchronizes third party integrated clinical applications 202 and reporting applications 203 in the same manner. For example, measurements performed are also required to be synchronized between multiple application windows which is also handled with native layer communication between application windows which displays the same measurements. Synchronization of clinical information between multiple windows can be simplified by diagnostic viewer 100 in such a way that there is no inter-process communication needed for application windows. Rather, each window can communicate with its child or parent window directly thereby eliminating potential communication gaps, timing issues, or latency. This direct communication can also ensure both sender and receiver windows in communication directly exchange information and acknowledgement without needing to have any additional communication for the acknowledgement aspect of the communication.

Communication between related applications windows can be performed using designated interfaces registered to each window. For example, a native image viewer window 101 can have interfaces of a Power Jacket window 103 and an Advanced Reporting window 103 to communicate with the corresponding application (e.g., Power Jacket 112, Advanced Reporting 113, or other suitable applications). The interfaces can be registered to each window as part of the settings relationship between them. As each window can have a native part which is the window container 103 and web part which is the UI layer (e.g., Power Jacket 112, Advanced Reporting 113, or other suitable applications), communication between windows is also based on which layer needs to talk to which layer. For example, if a native container layer of one window needs to communicate with a native layer of another window, an interface call can occur within a native address space. If a web layer of one window needs to communicate to a web layer of another window, the interface call can occur in both the web address space and the native address space.

Diagnostic viewer 100 can also allow radiologists and cardiologists to open multiple studies side-by-side as tabs and can perform reading and dictation, using dictation systems 204, of multiple studies by switching tabs. This can provide greater flexibility in interruption workflow where the user does not need to close and re-open the study 3 (e.g., 3A and 3B) while saving the study 3 (e.g., 3A and 3B) and the restoring to a previous state to continue with dictation, using dictation systems 204. When the user switches from one study 3 (e.g., 3A and 3B) to another, related application windows, e.g., Power Jacket, can also switch to a new study 3 (e.g., 3A and 3B) by hiding a currently displayed related application window and showing a new related application window corresponding to the new study 3 (e.g., 3A and 3B). The parent-child relationship of window management makes this transition easier without any ambiguity. Integrated external dictation system application windows 204 can also be updated by saving previous study reports as a draft and switching to a new study report. There are no technical limits on how many studies can be opened at a time and the memory management system of diagnostic viewer will make sure memory utilization is under the desired limits while working with multiple studies. This involves storing least used study images 1 (e.g., 1A-1H) to the disc memory where primary memory will be utilized for images 1 (e.g., 1A-1H) belong to the active study 3 (e.g., 3A and 3B). Each tab can have a patient banner in which patient information, e.g., patient name, gender, age, medical record number, or other suitable patient information, can be displayed to uniquely identify the study 3 (e.g., 3A and 3B). Each tab has a close button to close the specific study 3 (e.g., 3A and 3B).

In the case of the existing zero viewer implementation, the applications can run in the web browser where the existing zero viewer implementation requires additional middleman application/framework when it is required to communicate with third party clinical/reporting applications 202, 203. This always poses challenges in performance, stability and serviceability. The diagnostic viewer 100 can eliminate the need for additional middleman and instead can communicate with the thirds party clinical/reporting applications 202, 203 directly, irrespective of whether the application requires web integration or native integration. In addition to clinical/reporting applications 202, 203, several applications like external RIS worklist 201 communicate with diagnostic viewer 100 (for example, RIS worklist 201 launch a DICOM study 3 (e.g., 3A and 3B) in Diagnostic Client by executing a preconfigured WebQuery URL) similarly irrespective of whether such system has web integration or native integration.

When it is required to burn DICOM images of the study 3 (e.g., 3A and 3B) into external storage medium 67 like compact discs (CDs), in the current zero viewer, the current zero viewer requires downloading all DICOM images 1 (e.g., 1A-1H) to the workstation before it can start to burn the content to external storage medium, which takes considerable wait time for the user. The diagnostic viewer 100 already has DICOM content available in the workstation 60 and thus the system can directly burn the content to the external storage medium 67 where user gets the operation finished quicker.

The diagnostic viewer 100 can also exchange the displayed images 1 (e.g., 1A-1H) from Image Viewer 124 to external third-party applications 200 (e.g., Microsoft PowerPoint), by utilizing the native drag-drop mechanism offered by operating system. The current zero viewer implementation cannot do this due to a sandboxed browser environment. The diagnostic viewer 100 can also connect and exchange information with at least one printer 68 connected to workstation 60.

Diagnostic viewer 100 can provide offline workflow. For example, an authorized user can download an imaging study 3 (e.g., 3A and 3B) and other required information to display them offline. The information other than the imaging study 3 (e.g., 3A and 3B) being downloaded includes Java script/HTML assets, user settings, reading protocol etc. This downloaded content can be opened in diagnostic viewer 100 in offline mode where network connectivity to server is not required. Diagnostic viewer 100 can also include anonymization of the downloaded imaging study 3 (e.g., 3A and 3B) to make sure it is protected from PHI information and traceability is being exposed.

Figure 9:
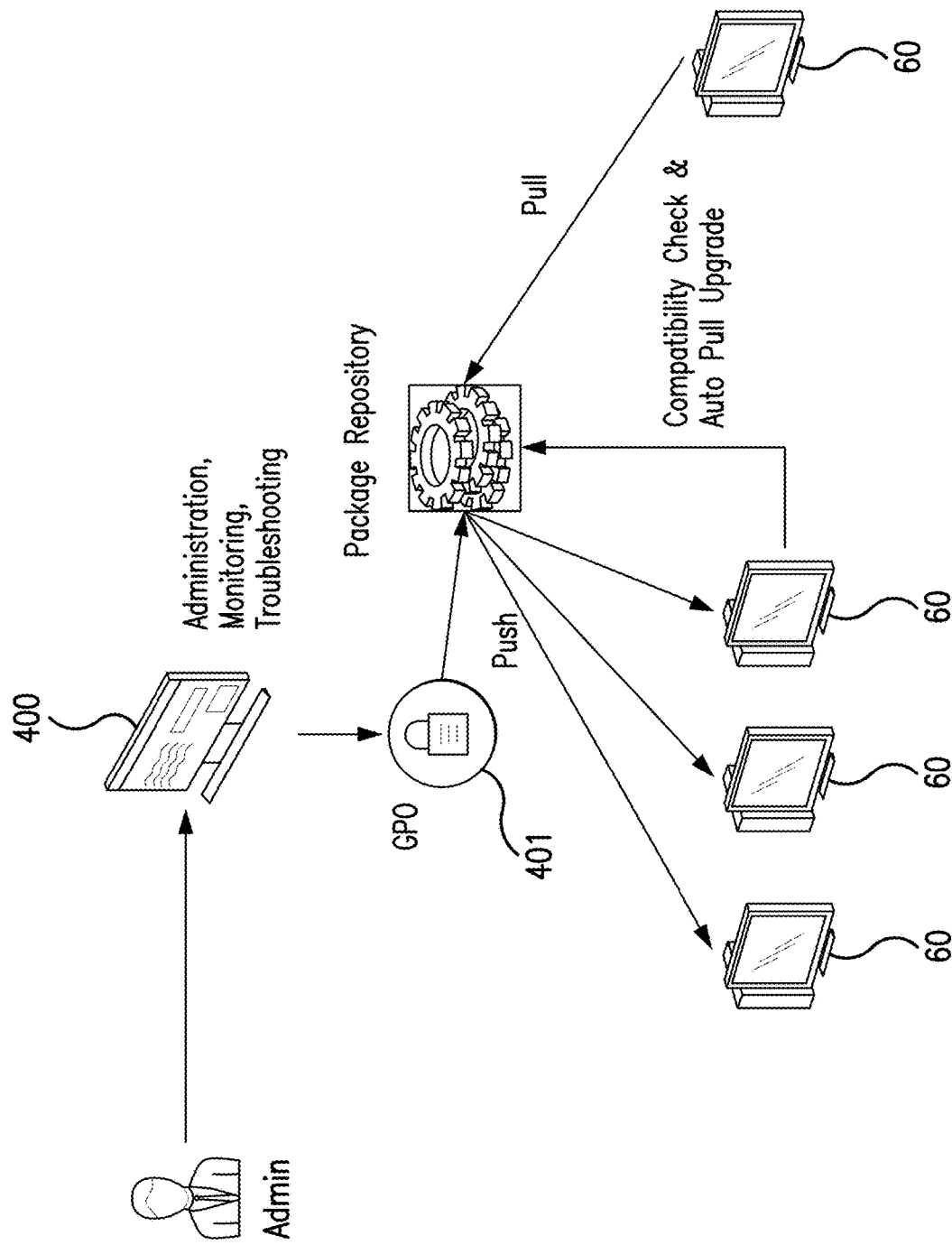
FIG. 9 shows the architecture of a system for providing administrative support for an image viewing application, in accordance with the disclosed subject matter.

Referring to FIG. 9 for purpose of illustration and not limitation, the diagnostic viewer 100 can support multiple deployment methods to choose from based on need of the user. For example, manual installation by downloading the package from the server 30 and application installation by administrator 400 from remote location by pushing the application through group policy software deployment mechanism 401. For example, a group policy can be used to remotely install software by assigning a program distribution users or computers, or pushing software to users (for example when the user logs into the system), as known in the art. Once deployed, the diagnostic viewer 100 can automatically detect updates by monitoring server 30 and upgrade automatically with user confirmation.

The diagnostic viewer 100 can post its health statistics which can include performance data (e.g., initial display performance, network speed, caching performance, decoding performance, rendering performance), workstation resource utilization, and critical error reports to server 30 which can be available to monitor from central administrative page 400. The administrative page 400 can display a list of all connected workstations classified based its physical location (for example, on premise v/s remote). Each workstation 60 will have an indicator to show its health and connectivity status. Color coding can be used in the status indicator to show whether the workstation 60 is stable or needs troubleshooting. Authorized users can click on each workstation 60 to expand the display area where recent heath statistics recorded by the workstation 60 will be displayed.

Authorized users can perform various operations using the administrative page 400 as part of troubleshooting the workstation 60, without physically reaching out to the workstation 60. For example, an administrator could work in a data center with the workstation 60 in a different location (e.g., a different room, building, city, state, or country). Users can upload detailed log files to the server 30 to analyze any potential issues with the workstation 60. The log files can include various application logs, performance logs and operating system logs, or other suitable log files. To get more detailed log information, including operational logs and TCP layer communication logs, the authorized users can turn troubleshooting mode ON and then upload the logs to the server 30.

Figure 10:
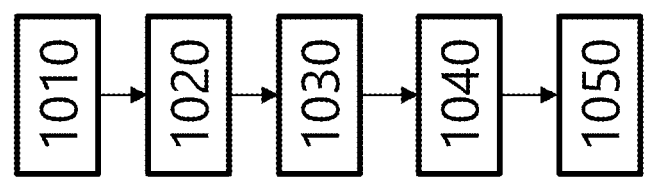
FIG. 10 is a flowchart illustrating how to render images on a device, in accordance with the disclosed subject matter.
Figure 10:
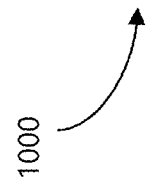

FIG. 10 illustrates an example method 1000 for rendering images on a device. The method can begin at step 1010 where the method can include initiating an image viewing application. At step 1020 the method can include downloading, in the image viewing application, a plurality of unrendered image files stored in a server memory. At step 1030 the method can include rendering, in the image viewing application, the plurality of unrendered image files using one or more device processors to generate a plurality of rendered image files. At step 1040 the method can include displaying, in the image viewing application, the plurality of rendered image files in at least one image window. At step 1050 the method can include rendering, in the image viewing application, at least one server application in at least one native window container, wherein the at least one server application is stored in the server memory and processed in the one or more server processors. Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates an example method for rendering images on a device including the particular steps of the method of FIG. 10, this disclosure contemplates any suitable method for rendering images on a device including any suitable steps, which can include all, some, or none of the steps of the method of FIG. 10, where appropriate. Furthermore, although this disclosure describes and illustrates particular components, devices, or systems carrying out particular steps of the method of FIG. 10, this disclosure contemplates any suitable combination of any suitable components, devices, or systems carrying out any suitable steps of the method of FIG. 10.

Figure 11:
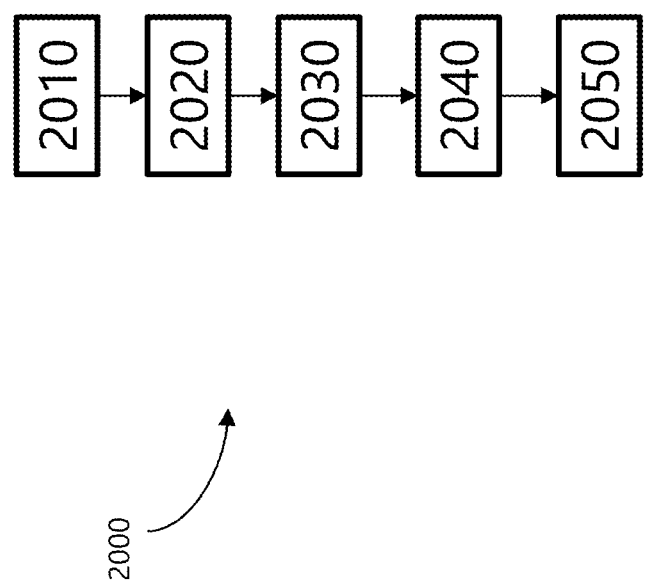
FIG. 11 is a flowchart illustrating a method for rendering images on a device, in accordance with the disclosed subject matter.

FIG. 11 illustrates an example method 2000 for rendering images on a device. The method can begin at step 2010, where the method can include initiating an image viewing application operating on the device. At step 2020 the method can include downloading, in the image viewing application, a plurality of unrendered image files, wherein the plurality of unrendered image files are assigned a priority value based on when the plurality of image files are to be displayed. At step 2030 the method can include storing, in the image viewing application, the plurality of unrendered image files downloaded in at least one of a first device memory and a second device memory, wherein the plurality of unrendered image files are stored in the at least one of the first device memory and the second device memory according to the assigned priority value. At step 2040 the method can include rendering, in the image viewing application, the plurality of unrendered image files based on the assigned priority value using at least one device processor, wherein if the plurality of unrendered image files having a predetermined priority value need to be displayed before downloading has completed, the rendering occurs in at least one processor of a server electrically coupled to the image viewing application. At step 2050 the method can include displaying the plurality of rendered image files, in the image viewing application, based on the assigned priority value, wherein the second device memory transfers at least one of the plurality of unrendered image files to the first device memory based on the assigned priority value and available storage space in the first device memory. In accordance with the disclosed subject matter, the method can repeat one or more steps of the method of FIG. 11, where appropriate. Although this disclosure describes and illustrates particular steps of the method of FIG. 11 as occurring in a particular order, this disclosure contemplates any suitable steps of the method of FIG. 11 occurring in any suitable order. Moreover, although this disclosure describes and illustrates an example method for rendering images on a device including the particular steps of the method of FIG. 11, this disclosure contemplates any suitable method for rendering images on a device including any suitable steps, which can include all, some, or none of the steps of the method of FIG. 11, where appropriate. Furthermore, although this disclosure describes and illustrates particular components, devices, or systems carrying out particular steps of the method of FIG. 11, this disclosure contemplates any suitable combination of any suitable components, devices, or systems carrying out any suitable steps of the method of FIG. 11.

Figure 12:
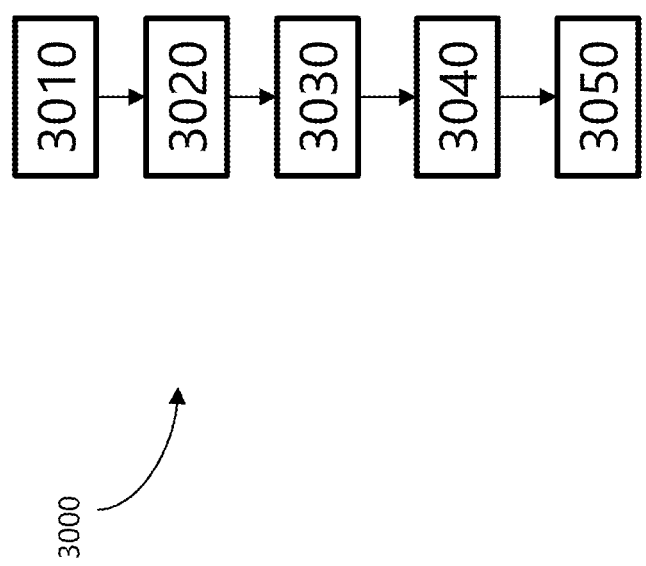
FIG. 12 is a flowchart illustrating a method for rendering images on a device, in accordance with the disclosed subject matter.

FIG. 12 illustrates an example method 3000 for rendering images on a device. The method can begin at step 3010, where the method can include initiating an image viewing application operating on a device. At step 3020 the method can include downloading, in the image viewing application, at least one first unrendered image file. At step 3030 the method can include storing, in the image viewing application, the at least one first unrendered image file downloaded in at least one of a first device memory and a second device memory. At step 3040 the method can include rendering, in the image viewing application, the at least one first unrendered image file into an at least one first rendered image file using at least one device processor. At step 3050 the method can include displaying the at least one first rendered image file, in the image viewing application, wherein the display of the at least one rendered image file is controlled through movement of a pointing device, wherein the image viewing application receives input data from the device about movement of the pointing device. In accordance with the disclosed subject matter, the method can repeat one or more steps of the method of FIG. 12, where appropriate. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates an example method for rendering images on a device including the particular steps of the method of FIG. 12, this disclosure contemplates any suitable method for rendering images on a device including any suitable steps, which can include all, some, or none of the steps of the method of FIG. 12, where appropriate. Furthermore, although this disclosure describes and illustrates particular components, devices, or systems carrying out particular steps of the method of FIG. 12, this disclosure contemplates any suitable combination of any suitable components, devices, or systems carrying out any suitable steps of the method of FIG. 12.

Figure 13:
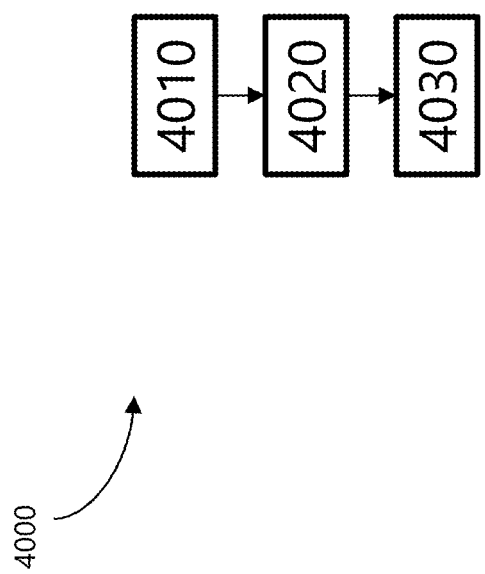
FIG. 13 is a flowchart illustrating a method for rendering images on a device, in accordance with the disclosed subject matter.

FIG. 13 illustrates an example method 4000 for rendering images on a device. The method can begin at step 4010, where the method can include initiating an image viewing application operating on a device. At step 4020 the method can include launching, in the image viewing application, a plurality of windows, the plurality of windows configured to run an image viewer window and at least one application window. At step 4030 the method can include establishing, in the image viewing application, a settings relationship between the plurality of windows on the device, wherein the plurality of windows are assigned relationships configured to synchronize content across the plurality of windows, wherein the image viewer window comprises a first communication interface registered to the application window based on the settings relationship, wherein the first application window comprises a first window container operated by the device and a first web interface layer operated by a first server electrically coupled to the device, wherein the image viewer window is operated by the device, and wherein the first communication interface is configured to operate within the device when communicating between the image viewer window and the window container. In accordance with the disclosed subject matter, the method can repeat one or more steps of the method of FIG. 13, where appropriate. Although this disclosure describes and illustrates particular steps of the method of FIG. 13 as occurring in a particular order, this disclosure contemplates any suitable steps of the method of FIG. 13 occurring in any suitable order. Moreover, although this disclosure describes and illustrates an example method for rendering images on a device including the particular steps of the method of FIG. 13, this disclosure contemplates any suitable method for rendering images on a device including any suitable steps, which can include all, some, or none of the steps of the method of FIG. 13, where appropriate. Furthermore, although this disclosure describes and illustrates particular components, devices, or systems carrying out particular steps of the method of FIG. 13, this disclosure contemplates any suitable combination of any suitable components, devices, or systems carrying out any suitable steps of the method of FIG. 13.

FIG. 14 illustrates an example method 5000 for rendering images on a device. The method can begin at step 5010, where the method can include initiating an image viewing application operating on a device. At step 5020 the method can include launching, in the image viewing application, a first instance comprising a plurality of windows, the plurality of windows configured to run at least an image viewer window and an application window. At step 5030 the method can include establishing, in the image viewing application, a settings relationship between the plurality of windows on the device, wherein the plurality of windows are assigned relationships configured to synchronize content across the plurality of windows. At step 5040 the method can include launching, in the image viewing application, a second instance comprising a second plurality of windows, the second plurality of windows configured to run at least a second image viewer window and a second application window. At step 5050 the method can include establishing, in the image viewing application, a second settings relationship between the second plurality of windows on the device, wherein the second plurality of windows are assigned relationships configured to synchronize content across the second plurality of windows, wherein the image viewer window comprises a first communication interface registered to the application window based on the settings relationship, wherein the second image viewer window comprises a second communication interface registered to the second application window based on the settings relationship, wherein switching from the first instance to the second instance hides the at least one application window and displays the at least one second window. In accordance with the disclosed subject matter, the method can repeat one or more steps of the method of FIG. 14, where appropriate. Although this disclosure describes and illustrates particular steps of the method of FIG. 14 as occurring in a particular order, this disclosure contemplates any suitable steps of the method of FIG. 14 occurring in any suitable order. Moreover, although this disclosure describes and illustrates an example method for rendering images on a device including the particular steps of the method of FIG. 14, this disclosure contemplates any suitable method for rendering images on a device including any suitable steps, which can include all, some, or none of the steps of the method of FIG. 14, where appropriate. Furthermore, although this disclosure de-scribes and illustrates particular components, devices, or systems carrying out particular steps of the method of FIG. 14, this disclosure contemplates any suitable combination of any suitable components, devices, or systems carrying out any suitable steps of the method of FIG. 14.

The subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or may be included in, one or more separate physical components or media (e.g., multiple CDs, disks, or other storage devices).

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA or an ASIC. The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program can, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC.

Processors suitable for the execution of a computer program can include, by way of example and not by way of limitation, both general and special purpose microprocessors. Devices suitable for storing computer program instructions and data can include all forms of non-volatile memory, media and memory devices, including by way of example but not by way of limitation, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Additionally, as described above in connection with certain embodiments, certain components can communicate with certain other components, for example via a network, e.g., a local area network or the internet. To the extent not expressly stated above, the disclosed subject matter is intended to encompass both sides of each transaction, including transmitting and receiving. One of ordinary skill in the art will readily understand that with regard to the features described above, if one component transmits, sends, or otherwise makes available to another component, the other component will receive or acquire, whether expressly stated or not.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for rendering images on a device, the method comprising:
   initiating an image viewing application operating on a device;
   downloading, in the image viewing application, at least one first unrendered image file;
   storing, in the image viewing application, the at least one first unrendered image file downloaded in at least one of a first device memory and a second device memory;
   rendering, in the image viewing application, the at least one first unrendered image file into an at least one first rendered image file using at least one device processor;
   displaying the at least one first rendered image file, in the image viewing application, wherein the display of the at least one rendered image file is controlled through movement of a pointing device, wherein the image viewing application receives input data from the pointing device regarding movement of the pointing device and wherein the image viewing application tracks the movement of the pointing device to predict an at least one second unrendered image file to be displayed after the at least one first rendered image file;
   downloading, in the image viewing application, the at least one second unrendered image file;
   storing, in the image viewing application, the at least one second unrendered image file downloaded in at least one of the first device memory and the second device memory;

rendering, in the image viewing application, the at least one second unrendered image file into an at least one second rendered image file using the at least one device processor; and displaying the at least one second rendered image file, in the image viewing application.

2. The method of claim 1, wherein the pointing device is a mouse connected to the device.

3. The method of claim 1, wherein the movement of the pointing device comprises one of at least a relative movement and an absolute movement of the pointing device.

4. The method of claim 1, wherein the plurality of unrendered image files are assigned a priority value based on when the plurality of unrendered image files are to be displayed, wherein the plurality of unrendered image files are stored in the at least one of the first device memory and the second device memory according to the assigned priority value, and wherein the plurality of unrendered image files are rendered based on the assigned priority value.

5. The method of claim 1, wherein the image viewing application is configured to scroll between the at least one first rendered image file and the at least one second rendered image file.

6. The method of claim 1, wherein the movement of the pointing device comprises a scroll of a wheel.

7. The method of claim 1, wherein the image viewing application is configured to transfer the at least one first unrendered image file from at least one of the first device memory and the second device memory.

8. A system for rendering images on a device, the system comprising:
a device having one or more device processors and a device memory coupled to the device processors comprising instructions executable by the device processors, the device processors being operable when executing the instructions to:
  initiate an image viewing application operating on a device;
  download, in the image viewing application, at least one first unrendered image file;
  store, in the image viewing application, the at least one first unrendered image file downloaded in at least one of a first device memory and a second device memory;
  render, in the image viewing application, the at least one first unrendered image file into an at least one first rendered image file using at least one device processor; and
  display the at least one first rendered image file, in the image viewing application, wherein the display of the at least one rendered image file is controlled through movement of a pointing device, wherein the image viewing application receives input data from the pointing device regarding movement of the pointing device and wherein the image viewing application tracks the movement of the pointing device to predict an at least one second unrendered image file to be displayed after the at least one first rendered image file;
  download, in the image viewing application, the at least one second unrendered image file;
  store, in the image viewing application, the at least one second unrendered image file downloaded in at least one of the first device memory and the second device memory;
  render, in the image viewing application, the at least one second unrendered image file into an at least one second rendered image file using the at least one device processor; and
  display the at least one second rendered image file, in the image viewing application.

9. The system of claim 8, wherein the pointing device is a mouse connected to the device.

10. The system of claim 8, wherein the movement of the pointing device comprises one of at least a relative movement and an absolute movement of the pointing device.

11. The system of claim 8, wherein the plurality of unrendered image files are assigned a priority value based on when the plurality of unrendered image files are to be displayed, wherein the plurality of unrendered image files are stored in the at least one of the first device memory and the second device memory according to the assigned priority value, and wherein the plurality of unrendered image files are rendered based on the assigned priority value.

12. The system of claim 8, wherein the image viewing application is configured to scroll between the at least one first rendered image file and the at least one second rendered image file.

13. The method of claim 8, wherein the movement of the pointing device comprises a scroll of a wheel.

14. The method of claim 8, wherein the image viewing application is configured to transfer the at least one first unrendered image file from at least one of the first device memory and the second device memory.

* * * * *